United States Patent
Battersby

(10) Patent No.: US 9,677,123 B2
(45) Date of Patent: Jun. 13, 2017

(54) DEGENERATE NUCLEOBASE ANALOGS

(75) Inventor: Thomas R. Battersby, El Cerrito, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 24 days.

(21) Appl. No.: 12/282,180

(22) PCT Filed: Mar. 7, 2007

(86) PCT No.: PCT/US2007/063483
§ 371 (c)(1),
(2), (4) Date: Sep. 9, 2008

(87) PCT Pub. No.: WO2007/106690
PCT Pub. Date: Sep. 20, 2007

(65) Prior Publication Data
US 2010/0055798 A1    Mar. 4, 2010

Related U.S. Application Data

(60) Provisional application No. 60/782,385, filed on Mar. 15, 2006.

(51) Int. Cl.
C07H 21/04 (2006.01)
C12Q 1/68 (2006.01)

(52) U.S. Cl.
CPC ......... C12Q 1/6813 (2013.01); C12Q 1/6876 (2013.01); Y10T 436/143333 (2015.01)

(58) Field of Classification Search
USPC .............................................. 536/22.1; 435/6
See application file for complete search history.

(56) References Cited

U.S. PATENT DOCUMENTS

| | | | |
|---|---|---|---|
| 5,859,221 A | | 1/1999 | Cook et al. |
| 5,955,443 A | | 9/1999 | Bennett et al. |
| 6,140,496 A | * | 10/2000 | Benner .................. 536/27.1 |
| 6,743,905 B2 | * | 6/2004 | Woo et al. ................ 536/23.1 |
| 7,008,770 B1 | * | 3/2006 | Berlin ..................... 435/6 |
| 7,741,294 B1 | * | 6/2010 | Benner .................. 514/23 |
| 2003/0077608 A1 | * | 4/2003 | Coull et al. .............. 435/6 |

FOREIGN PATENT DOCUMENTS

| | | |
|---|---|---|
| WO | WO 2004/111266 A1 * | 12/2004 |
| WO | 2005001091 | 1/2005 |
| WO | 2005035545 | 4/2005 |

OTHER PUBLICATIONS

Lin, P.K.T. et al. Synthesis of oligodeoxyribonucleotides containing degenerate bases and their use as primers in the polymerase chain reaction. Nucleic Acids Research, vol. 20(19), p. 5149-5152, 1992.*
Stratagene Catalog. gene characterization kits. Stratagene Catalog, p. 39, 1988.*
EP Supplementary Search report for EP app. No. 07758070 dated Oct. 14, 2013.
Margraf, Rebecca L. et al; "Masking Selected Sequence Variation by Incorporating Mismatches Into Melting Analysis Probes"; Human Mitation, 27(3): 269-278, (2005).
Guo, Z. et al; "Enhanced discrimination of single nucleotide polymorphisms by artificial mismatch hybridization"; Nature Biotechnology, 15: 331-335, (1997).
Kong, Thoo Lin P. et al; "Synthesis of oligodeoxyribonucleotides containing degenerate bases and their use as primers in the polymerase chain reaction"; Nucleic Acids Research, 20(19): 5149-5152, (1992).
Jurczyk, Simona C. et al; "Synthesis of Oligonucleotides Containing 2'-Deoxyisoguanosine and 2'-Deoxy-5-methylisocytidine Using Phosphoramidite Chemistry"; Verlag Helvetica Chimica Acta,; 81:793-811(1998).

* cited by examiner

*Primary Examiner* — Prabha Chunduru

(57) ABSTRACT

The present invention relates to novel degenerate nucleobase analogs and degenerate nucleobase oligomers derived therefrom, and methods of using such degenerate nucleobase oligomers.

10 Claims, 2 Drawing Sheets

DEGENERATE NUCLEOBASE ANALOGS

CROSS REFERENCE TO RELATED APPLICATION

This application claims the benefit of the filing date of U.S. Provisional Patent Application No. 60/782,385, filed Mar. 15, 2006, the disclosure of which is incorporated, in its entirety, by this reference.

FIELD OF THE INVENTION

The present invention relates generally to the field of nucleic acid identification, and more particularly to oligonucleotides used to identify nucleic acid analytes.

BACKGROUND

A wide variety of biological research and clinical techniques utilize synthetic nucleic acid or other nucleobase polymer probes and primers for the detection, quantification, and characterization of the genetic basis of inherited and infectious diseases. Such techniques typically rely upon hybridization of the nucleic acid probes and primers to complementary regions of DNA or RNA that characterize the disease.

Probe based assays are the basis of all studies of gene expression where selectivity for specific nucleotide species is required. Nucleic acid or other nucleobase polymer probes have long been used clinically to analyze samples for the presence of nucleic acid from infectious agents, such as bacteria, fungi, virus or other organisms, and in examining genetically-based diseases.

Nucleic acid amplification assays, using oligonucleotide primers, comprise an important class of sequence-specific detection methods used in modern biological analyses, with diverse applications in diagnosis of human disease, human identification, identification of microorganisms, paternity testing, virology, and DNA sequencing. The polymerase chain reaction (PCR) amplification method allows for the production and detection of target nucleic acid sequences with great sensitivity and specificity. PCR methods have proliferated and been adapted to form the foundation of numerous biological applications, including cloning methods, analysis of gene expression, DNA sequencing, genetic mapping, drug discovery, and numerous other applications. Methods for detecting a PCR product (i.e., an amplicon) using a nucleobase oligomer probe capable of hybridizing with the target sequence or amplicon are well known in the art.

Although such methodologies are made possible by the binding specificity of probes and primers to a nucleic acid template, the presence of polymorphic variations in a particular template may also limit the utility of specific probes, since differences between the nucleic acid sequence of the probe and the nucleic acid sequence of the template (as a result of polymorphic variation in the template) may prevent the probe from hybridizing to the template. One approach to this problem has been to design different sets of probes complementary to each polymorphic variant. The use of degenerate probe sets, however, is often technically and economically prohibitive. In addition, degenerate probe sets are ineffective in identifying unknown polymorphic variations not contemplated by the degenerate probe set.

Another approach to discriminating between nucleic acid templates having multiple polymorphic variations has been to emphasize differences attributable to one particular polymorphic site by deliberately introducing mismatches near the polymorphic site of interest using universal nucleobases that do not include hydrogen bond donor or acceptor groups (See, e.g., Margraf et al., Masking selected sequence variation by incorporating mismatches into melting probes, Hum. Mutat. 0:1-10 (2006)).

Accordingly, there is a need for improved methods and reagents for detection, quantification and characterization of nucleic acid templates having polymorphic variation.

SUMMARY OF THE INVENTION

The present invention relates to improved methods and reagents for detection, quantification and characterization of nucleic acid templates having polymorphic variation. More particularly, the present invention relates to nucleic acid probes and primers containing a degenerate nucleobase analog capable of non-selective hybridization opposite multiple natural nucleobases.

The degenerate nucleic acid probes and primers of the present invention will include degenerate nucleobase analogs having ambiguous base pairing properties, capable of pairing non-selectively opposite two or more nucleobase constituents of a nucleic acid duplex, which will result in minimal destabilization of a nucleic acid duplex when opposite these target nucleobases. Other desirable requirements include ability to function in polymerase replication and other enzymatic recognition.

The nucleobase oligomers of the invention are useful for hybridization to a polynucleotide template having multiple polymorphic loci (sites where polymorphisms give rise to multiple genetic variants). When multiple polymorphic loci are present in close proximity, particularly within a region to which one wishes to have an oligonucleotide probe or primer hybridize, the presence of one or more polymorphic locus may complicate detection, identification or characterization of another polymorphic locus. For example, a common method of detecting a particular allele utilizes melting curve analysis to determine the particular nucleotide sequence at a specific target polymorphic locus. Melting curve analysis utilizes a hybridization probe that, typically, is exactly complementary to the nucleotide sequence of one allele at the target polymorphic locus, but differs from other known alleles at that locus. The hybridization probe thus binds to one allele with higher affinity than the other alleles, resulting in the probe dissociating from the polymorphic locus at a different, and distinctive, melting temperatures. If, however, the binding region of the polynucleotide template has other polymorphic sites, those other polymorphic sites may alter the melting curve profile and confound accurate detection and characterization of the target polymorphic locus. The materials and methods of the present invention permit accurate detection and characterization of a target polymorphic locus, even when one or more other polymorphic loci are located in close proximity.

Accordingly, one aspect of the invention relates to a degenerate nucleobase oligomer corresponding to a polynucleotide template having a first polymorphic site characterized by multiple nucleobase variations and a second polymorphic site characterized by multiple nucleobase variations. The oligomer comprises a degenerate nucleobase complementary to multiple nucleobase variations at the first polymorphic site, and a base-specific nucleobase complementary to a single nucleobase variation at the second polymorphic site, wherein the base-specific nucleobase is characteristic of a single allele of the polynucleotide template.

Another aspect of the invention relates to a polynucleotide duplex comprising a degenerate nucleobase oligomer hybridized to a corresponding multi-allelic polynucleotide template. The polynucleotide template comprises a first polymorphic site characterized by multiple nucleobase variations and a second polymorphic site characterized by multiple nucleobase variations, and the degenerate nucleobase oligomer comprises a degenerate nucleobase complementary to multiple nucleobase variations of the first polymorphic site, and a base-specific nucleobase complementary to a single nucleobase variation at the second polymorphic site, wherein the base-specific nucleobase is characteristic of a single allele of the polynucleotide template.

Another aspect of the invention relates to a method for preparing a degenerate nucleobase oligomer corresponding to a binding region of a polynucleotide template, comprising: determining the nucleotide sequence of a multi-allelic polynucleotide template having a first polymorphic site characterized by multiple nucleobase variations and a second polymorphic site characterized by multiple nucleobase variations, and preparing a degenerate nucleobase oligomer comprising a degenerate nucleobase complementary to multiple nucleobase variations at the first polymorphic site, and a base-specific nucleobase complementary to a single nucleobase variation at the second polymorphic site, wherein the base-specific nucleobase is characteristic of a single allele of the polynucleotide template.

Another aspect of the invention relates to a method for hybridizing a degenerate nucleobase oligomer to a polynucleotide template, comprising: determining the nucleotide sequence of a multi-allelic polynucleotide template having a first polymorphic site characterized by multiple nucleobase variations and a second polymorphic site characterized by multiple nucleobase variations; preparing a degenerate nucleobase oligomer comprising a degenerate nucleobase complementary to multiple nucleobase variations at the first polymorphic site, and a base-specific nucleobase complementary to a single nucleobase variation at the second polymorphic site, wherein the base-specific nucleobase is characteristic of a single allele of the polynucleotide template; and hybridizing the degenerate nucleobase oligomer to the polynucleotide template, under conditions wherein each degenerate nucleobase oligomer hybridizes non-selectively to multiple nucleobase variations at the first polymorphic site.

Another aspect of the invention relates to a method for amplifying a multi-allelic polynucleotide template, comprising: providing a multi-allelic polynucleotide template having a first polymorphic site characterized by multiple nucleobase variations and a second polymorphic site characterized by multiple nucleobase variations; providing a degenerate nucleobase oligomer comprising a degenerate nucleobase complementary to multiple nucleobase variations at the first polymorphic site, and a base-specific nucleobase complementary to a single nucleobase variation at the second polymorphic site, wherein the base-specific nucleobase is characteristic of a single allele of the polynucleotide template; hybridizing the degenerate nucleobase oligomer to the polynucleotide template, under conditions wherein each degenerate nucleobase oligomer hybridizes non-selectively to multiple nucleobase variations at the first polymorphic site to form a duplex; and subjecting the duplex to polymerase chain reaction under conditions sufficient to selectively amplify a polynucleotide template having the single nucleobase variation corresponding to the base-specific nucleobase.

Another aspect of the invention relates to a method for determining the genotype of a multi-allelic polynucleotide template, comprising: providing a multi-allelic polynucleotide template having a first polymorphic site characterized by multiple nucleobase variations and a second polymorphic site characterized by multiple nucleobase variations; providing a degenerate nucleobase oligomer comprising a degenerate nucleobase complementary to multiple nucleobase variations at the first polymorphic site, and a base-specific nucleobase complementary to a single nucleobase variation at the second polymorphic site, wherein the base-specific nucleobase is characteristic of a single allele of the polynucleotide template; hybridizing the degenerate nucleobase oligomer to the polynucleotide template, under conditions wherein each degenerate nucleobase oligomer hybridizes non-selectively to multiple nucleobase variations at the first polymorphic site; and disassociating the nucleobase oligomer from the polynucleotide template under conditions sufficient to generate a melting curve profile of the duplex characteristic of the allele of the second polymorphic site having the single nucleobase variation corresponding to the base-specific nucleobase.

Another aspect of the invention relates to a method for quantitating the amount of nucleic acid analyte present in a sample, comprising: providing a nucleic acid analyte comprising a multi-allelic polynucleotide template having a first polymorphic site characterized by multiple nucleobase variations and a second polymorphic site characterized by multiple nucleobase variations; providing a degenerate nucleobase oligomer comprising a degenerate nucleobase complementary to multiple nucleobase variations at the first polymorphic site, and a base-specific nucleobase complementary to a single nucleobase variation at the second polymorphic site, wherein the base-specific nucleobase is characteristic of a single allele of the polynucleotide template; hybridizing the degenerate nucleobase oligomer to the polynucleotide template, under conditions wherein each degenerate nucleobase oligomer hybridizes non-selectively to multiple nucleobase variations at the first polymorphic site; and quantitatively detecting the amount of nucleic acid analyte present in the sample.

Another aspect of the invention relates to a kit for analyzing a nucleic acid analyte having a multi-allelic polynucleotide template with a first polymorphic site characterized by multiple nucleobase variations and a second polymorphic site characterized by multiple nucleobase variations, wherein the kit comprises: a degenerate nucleobase oligomer having a degenerate nucleobase complementary to multiple nucleobase variations at the first polymorphic site of the analyte, and a base-specific nucleobase complementary to a single nucleobase variation at the second polymorphic site, wherein the base-specific nucleobase is characteristic of a single allele of the polynucleotide template.

Another aspect of the invention relates to a degenerate nucleobase oligomer corresponding to a polynucleotide template having a polymorphic site, wherein the oligomer comprises a degenerate nucleobase complementary to multiple nucleobase variations at a polymorphic site and having a hydrogen bonding pattern of pyAAD or puDDA.

In some embodiments, the degenerate nucleobase oligomers of the invention may include a plurality of degenerate nucleobases, each of which is complementary to multiple nucleobase variations at a corresponding polymorphic site.

In some embodiments, the melting temperature of the degenerate nucleobase oligomer and the polynucleotide template is substantially equivalent to the melting temperature of a natural nucleobase oligomer and the polynucleotide template.

In some embodiments, the degenerate nucleobase of the oligomer is flanked by natural nucleobases.

In some embodiments, the hydrogen bonding pattern of the degenerate nucleobase of the oligomer is pyAAD or puDDA.

In some embodiments, the hydrogen bonding pattern of the degenerate nucleobase oligomer with a corresponding nucleobase of the polynucleotide template is puDDA:pyDAA, puDDA:pyADA, puDA_:pyAAD, or puADD:pyAAD.

In some embodiments, the degenerate nucleobase having a hydrogen bonding pattern of pyAAD is 5-methylisocytidine, isocytidine, or 2'-deoxy analogs thereof.

In some embodiments, the degenerate nucleobase having a hydrogen bonding pattern of puDDA is isoguanosine, 7-deazaisoguanosine, 7-deaza-8-azaisoguanosine, N6-(6-aminohexyl)isoguanosine, N6-(2-(1H,imidazol-4-yl)-ethyl)isoguanosine, N6-(N-(Dabcyl)-6-aminohexyl)isoguanosine, or 2'-deoxy analogs thereof.

In some embodiments, the allele-specific nucleobase hybridizes selectively to each allele of the target polymorphic locus.

In some embodiments, the allele-specific nucleobase is non-complementary to a single allele of the polymorphic locus.

In some embodiments, the allele-specific nucleobase is complementary to a single allele of the polymorphic locus.

The degenerate nucleobase oligomers of the present invention enable use of a single oligonucleotide, which can act equally well as a primer in PCR amplification or other replication of nucleic acid targets with variation of the template nucleic acid at specific positions. A single oligonucleotide can act equally well as a hybridization probe against nucleic acid targets with variation at specific positions.

The degenerate nucleobase oligomers of the present invention also enable identification of analyte nucleic acids with variation at specific positions in thermal denaturation (melting curve) analysis that would otherwise be confounded by a disparity in melting temperatures.

DETAILED DESCRIPTION OF THE INVENTION

Figure 1:
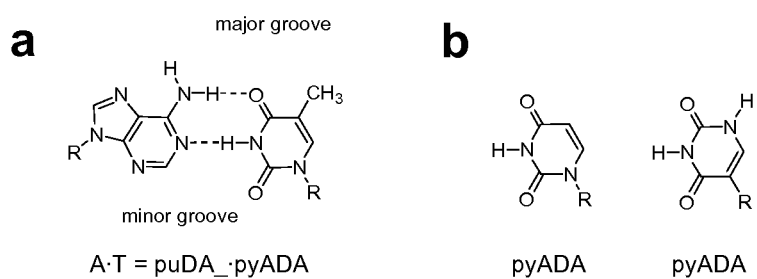
FIG. 1 shows the designation of nucleobases and analog nucleobases. (a) The analogs are either purine-like (pu) or pyrimidine-like (py). Upper case letters indicate the H-bonding pattern of acceptor (A) and donor (D) groups moving from the major to the minor groove. The nucleobase adenine, lacking a third H-bonding functional group, is designated puDA_. The nucleobase thymine is designated pyADA. (b) Alternative analog structures are possible for these designations. For example, pyADA analogs include uracil and pseudothymine.

Unless defined otherwise, technical and scientific terms used herein have the same meaning as commonly understood by one of ordinary skill in the art to which this invention belongs. Units, prefixes, and symbols may be denoted in their SI accepted form. Unless otherwise indicated, nucleic acids are written left to right in 5' to 3' orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic sequence discrepancy within the application, the figures control. One skilled in the art will recognize many methods and materials similar or equivalent to those described herein, which could be used in the practice of the present invention. The present invention is in no way limited to the methods and materials described. For purposes of the present invention, the following terms are defined below.

"Allele" means one of multiple alternate forms of a polynucleotide template having a particular nucleobase at a polymorphic site. The term "allele" is commonly used to refer to one of two alternate forms of a gene that have a common locus on homologous chromosomes (within a single organism, or among different organisms within a common species) and may be responsible for alternative traits. As used herein, the term "allele" is also used to refer to a particular polymorphic variant (nucleobase) at a polymorphic site of polynucleotide template. It is understood that the term "allele" may be used in reference to alternate forms of any type of polynucleotide template, including synthetic or recombinant polynucleotide templates, as well as natural polynucleotide templates (genes) derived from a natural source.

"Base-specific," as used in reference to a "base-specific" nucleobase, means the nucleobase is capable of selectively or specifically hybridizing to another nucleobase either by hydrogen bonding interactions that result from complementary base pairing or another mechanism of selection. A base-specific nucleobase may, for example, specifically hybridize to a particular base at a polymorphic site, such that hybridization is indicative of the presence and identity of the base at that site, and failure to hybridize is indicative of the absence of the base at that site. The term "base-specific" is also understood to encompass a base that specifically hybridizes to all but one base at a polymorphic site, such that hybridization is indicative of the presence of at least one of the bases to which it hybridizes, and failure to hybridize is indicative of the absence of all bases to which it hybridizes (and, inferentially, the presence and identity of the one base to which it does not hybridize). Natural nucleobases, for example, specifically hybridize to corresponding natural nucleobases according to Watson/Crick base pairing rules. Non-natural nucleobases may also serve as base-specific nucleobases, provided they are capable of hybridizing and disassociating in a manner capable of generating a melting curve distinctive of the nucleobase to which it hybridizes. Non-limiting examples of standard base pairing includes adenine base pairing with thymine or uracil and guanine base pairing with cytosine. Other non-limiting examples of base-pairing motifs include, but are not limited to: adenine base pairing with any of: 5-propynyl-uracil, 2-thio-5-propynyl-uracil, 2-thiouracil or 2-thiothymine; guanine base pairing with any of: 5-methylcytosine or pseudoisocytosine; cytosine base pairing with any of: hypoxanthine, N9-(7-deaza-guanine) or N9-(7-deaza-8-aza-guanine); thymine or uracil base pairing with any of: 2-aminopurine, N9-(2-amino-6-chloropurine) or N9-(2,6-diaminopurine); isocytosine or 5-methylisocytosine pairing with any of: isoguanine, 7-deazaisoguanine or 7-deaza-8-aza-isoguanine; or 2,4-diaminopyrimidine with any of: xanthosine or 7-deazaxanthosine. A base-specific nucleobase is said to be "characteristic of" a single allele of a polynucleotide template if hybridization of the nucleobase to that allele is indicative of the identity or distinguishing characteristics of the allele.

"Complementary" means that a nucleobase of a polynucleotide is capable of hybridizing to a corresponding nucleobase in a different polynucleotide. As used herein, the term "complementary" is not limited to canonical Watson-Crick base pairs with A/T, G/C and U/A. Thus, nucleobase pairs may be considered to be "complementary" if one or both of the nucleobases is a nucleobase other than A, G, C, or T, such as a universal or degenerate nucleobase. A degenerate or universal nucleobase that is "complementary" to two or more corresponding nucleobases is considered to hybridize non-selectively to the two or more corresponding nucleobases. The term "complementary" also refers to antiparallel strands of polynucleotides (as opposed to a single nucleobase pair) that are capable of hybridizing. For example, the sequence 5'-AGTTC-3' (SEQ ID NO:2) is complementary to the sequence 5'-GAACT-3'. (SEQ ID NO:3). The term "complementary" is sometimes used interchangeably with "antisense." Thus, degenerate nucleobase oligomers are said to hybridize to a corresponding multi-allelic polynucleotide template. The term "complementary," as used in reference to two nucleotide sequences or two nucleobases, implies that the nucleotides sequences or nucleobases are "corresponding."

"Corresponding" means, as between two nucleotide sequences or two nucleobases within a sequence, having the same or nearly the same relationship with respect to position and complementarity, or having the same or nearly the same relationship with respect to structure, function, or genetic coding (for example, as between a gene and the "corresponding" protein encoded by the gene). For example, a nucleotide sequence "corresponds" to region of a polynucleotide template if the two sequences are complementary or have portions that are complementary. Similarly, a nucleobase of an oligomer "corresponds" to a nucleobase of a polynucleotide template when the two nucleobases occupy a position such that when the oligomer and the polynucleotide hybridize the two nucleobases pair opposite each other. The term "corresponding" is generally used herein in reference to the positional relationship between two polynucleotide sequences or two nucleobases. The term "corresponding" does not imply complementarity; thus, corresponding nucleobases may be complementary, or may be non-complementary.

"Degenerate nucleobase" means a nucleobase of an oligomer that is capable of hybridizing non-specifically and equivalently opposite a plurality of nucleobases at a corresponding position of a polynucleotide template, such as through hydrogen bond interactions. The base pairing interaction of a degenerate nucleobase opposite intended target nucleobases is considered equivalent or non-selective if the interactions are not substantially stabilizing or destabilizing relative to each other. Degenerate nucleobases will, therefore, result in pairings that are sufficiently equivalent that any differences in interaction of the degenerate nucleobase and any of the intended target nucleobases do not materially affect the duplex hybridization and/or disassociation, and either permit discrimination of the duplex on the basis of differences other than the degenerate nucleobase pairing or, alternatively, eliminate discrimination of the duplex on the basis of differences of the degenerate nucleobase pairing. A "universal nucleobase" means a nucleobase of an oligomer that is capable of hybridizing non-specifically and equivalently opposite any of the natural nucleobases at a corresponding position of a polynucleotide template.

"Duplex" means an intermolecular or intramolecular double-stranded portion of one or more nucleobase oligomers which is base-paired through Watson-Crick, Hoogsteen, or other sequence-specific interactions of nucleobases. Duplexes may also form with sequences that include degenerate nucleobase analogs. In one embodiment, a duplex may consist of a primer and a template strand. In another embodiment, a duplex may consist of a non-extendable nucleobase oligomer probe and a target strand. A "hybrid" means a duplex, triplex, or other base-paired complex of nucleobase oligomers interacting by base-specific interactions, i.e., Watson-Crick or Hoogsteen type interactions.

"Equivalent" or "equivalently" or "non-selective" or "non-selectively," as used in reference to hybridization of a degenerate nucleobase of an oligomer to multiple polymorphic variants at a corresponding nucleobase position of a polynucleotide template, means that the hybridization/dissociation (thermal denaturation) conditions attributable to the degenerate nucleobase and one variant, and the hybridization/dissociation conditions attributable to the degenerate nucleobase and another variant, are sufficiently similar that the melting temperature (Tm) of the duplex is not significantly affected, and does not result in downstream disparities that would adversely impact the ability to discriminate on the basis of other differences, or that would adversely impact the use of the oligomer as a hybridization probe or primer in a quantitative regime. By way of example, a degenerate nucleobase oligomer hybridizes equivalently and non-selectively to multiple polymorphic variants when melting curve analysis is able to detect and identify differences between the oligomer and the polynucleotide template that are not attributable to any differences between the Tm of the degenerate nucleobase and the various polymorphic variants. Also by way of example, a degenerate nucleobase oligomer hybridizes equivalently and non-selectively to multiple polymorphic variants when the oligomer is used in a quantitative regime and any differences between the Tm of the degenerate nucleobase and the various polymorphic variants does not materially impact the accuracy of the quantitative analysis.

"Hybridization" and "annealing" are used interchangeably and mean the base-pairing interaction of one nucleobase with another nucleobase, or one polynucleotide with another polynucleotide, that results in formation of a duplex or other higher-ordered structure. The primary interaction is base specific, i.e., A/T and G/C, by Watson/Crick and Hoogsteen-type hydrogen bonding between corresponding nucleobases, or by alternative hydrogen bonding patterns where one or more of the nucleobase pairs is a universal or degenerate nucleobase.

"Hydrogen bonding pattern" means the hydrogen bonding pattern of acceptor (A) and donor (D) groups of a pyrimidine or pyrimidine analog (py) and a purine or purine analog (pu) molecule, designated using the nomenclature of Benner (Lutz, et al., Differential discrimination of DNA polymerases for variants of the non-standard nucleobase pair between xanthosine and 2,4-diaminopyrimidine, two components of an expanded genetic alphabet, Nucleic Acids Res. 24:1308-1313 (1996) in order of the acceptor and donor group from the major groove to the minor groove. The bonding pattern nomenclature used herein adopts the convention of first designating a pyrimidine or pyrimidine analog with the lower case letters "py" and a purine or purine analog with the lower case letters "pu", followed by 0, 1, 2 or 3H-bonding functionalities designated by the upper case letters A or D, indicating the hydrogen bonding patterns of the various groups of the molecule as either A (acceptor) or D (donor). An underline (_) is used to designate the absence of a hydrogen donor or acceptor group.

A pyrimidine or analog (py) is used opposite two purines (adenine and guanine, in the case of natural DNA) such that the pyrimidine forms a "wobble" pair with one of the purines and a "reverse wobble" pair with the other purine. Similarly, a purine or analog (pu) is used opposite two pyrimidines (cytosine and uracil or thymine) such that the purine forms two hydrogen bonds in a "wobble" pair with one of the pyrimidines and two hydrogen bonds in a "reverse wobble" pair with the other pyrimidine. As shown in FIG. 1, the hydrogen bonding patterns of the natural purines are denoted as puDA (adenine) and puADD (guanine), and the hydrogen bonding patterns of the natural pyrimidines are pyDAA (cytosine) and pyADA (thymine/uracil). Thus, the notation representing cytosine-guanine bonding pattern is pyDAA-puADD, and the thymine/uracil-adenine bonding pattern is pyADA-puDA_.

Figure 2:
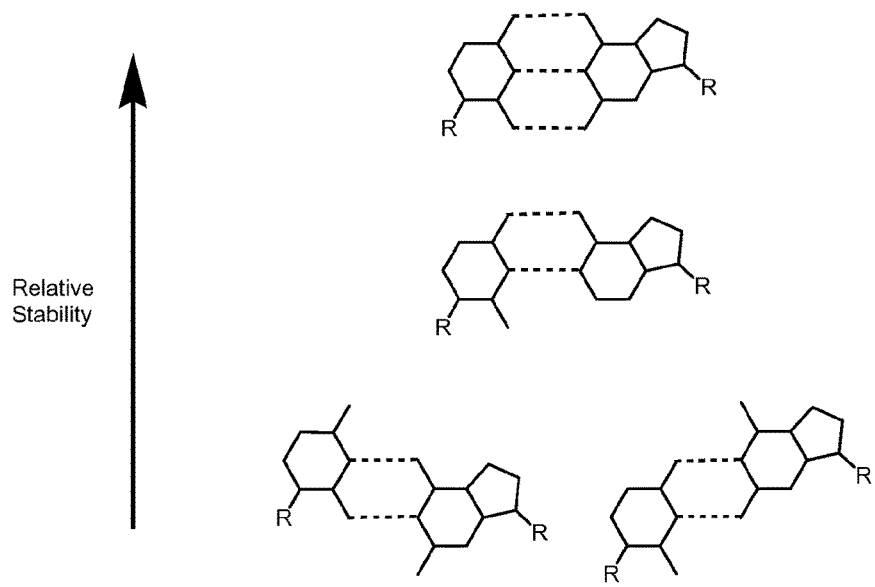
FIG. 2 illustrates the relative stabilities of purine-pyrimidine pairs in a DNA duplex. Watson-Crick pairs joined by three H-bonds (top) are generally more stabilizing than Watson-Crick pairs joined by two H-bonds (middle). Roughly equivalent are wobble and reverse wobble pairs joined by two H-bonds (bottom), which are generally less stabilizing than the Watson-Crick pairs.

The above notation can also be used to represent bonding patterns of degenerate bases. As shown in FIG. 2, the bonding pattern of a degenerate base paired with purine molecules is pyAAD. The hydrogen bonding patterns of the natural pyrimidines are pyDAA and pyADA; therefore, a degenerate base for these pyrimidines will have the hydrogen bonding pattern of puDDA. Degenerate purines forming wobble and reverse wobble conformations associated by two hydrogen bonds opposite, respectively, cytosine (pyDAA) and thymine (pyADA), will have the hydrogen bonding pattern of puDDA. Examples of puDDA nucleobases include isoguanine (iG), 7-deazaisoguanosine, 7-deaza-8-azaisoguanosine, N6-(6-aminohexyl)isoguanosine, N6-(2-(1H,imidazol-4-yl)-ethyl)isoguanosine, N6-(N-(Dabcyl)-6-aminohexyl)isoguanosine, and 2'-deoxy analogs thereof. Degenerate pyrimidines forming wobble and reverse wobble conformations associated by two hydrogen bonds opposite, respectively, adenine (puDA_) and guanine (puADD), will have the hydrogen bonding pattern of pyAAD. Examples of pyAAD nucleobases include 5-methylisocytidine, isocytidine (iC), and 2'-deoxy analogs thereof.

"Nucleobase" means any nitrogen-containing heterocyclic moiety capable of forming Watson-Crick-type hydrogen bonds and stacking interactions in pairing with a complementary nucleobase or nucleobase analog (i.e., derivatives of nucleobases) when that nucleobase is incorporated into a polymeric structure. "Heterocyclic" refers to a molecule with a ring system in which one or more ring atom is a heteroatom, e.g., nitrogen, oxygen, or sulfur (i.e., not carbon).

A large number of nucleobases, nucleobase analogs and nucleobase derivatives are known. Non-limiting examples of nucleobases include purines and pyrimidines, and modified forms, e.g., 7-deazapurine. Typical nucleobases are the naturally occurring nucleobases adenine, guanine, cytosine, uracil, thymine, and analogs (Seela, U.S. Pat. No. 5,446,139) of the naturally occurring nucleobases, e.g., 7-deazaadenine, 7-deazaguanine, 7-deaza-8-azaguanine, 7-deaza-8-azaadenine, inosine, nebularine, nitropyrrole (Bergstrom, J. Amer. Chem. Soc., 117:1201-1209 [1995]), nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine (Seela, U.S. Pat. No. 6,147,199), 7-deazaguanine (Seela, U.S. Pat. No. 5,990,303), 2-azapurine (Seela, WO 01/16149), 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, pyrazolo[3,4-D]pyrimidines, "PPG" (Meyer, U.S. Pat. Nos. 6,143,877 and 6,127,121; Gall, WO 01/38584), and ethenoadenine (Fasman (1989) in Practical Handbook of Biochemistry and Molecular Biology, pp. 385-394, CRC Press, Boca Raton, Fla.).

"Nucleobase oligomer" or "oligomer" as used herein refers to a polymer of covalently-joined monomeric nucleobase subunits. The term does not limit the nucleobase polymer to any particular length, as these terms encompass polymeric forms of any length. Typically, bases may be attached to a polymeric backbone structure in a "nucleobase oligomer" or "oligomer." An oligomer can be single-stranded or double-stranded, and can be complementary to the sense or antisense strand of a gene sequence, or any other nucleobase sequence. A nucleobase oligomer can hybridize with a complementary portion of a target polynucleotide to form a duplex, which can be a homoduplex or a heteroduplex. A nucleobase oligomer is typically short, for example but not exclusively, less than about 100 nucleobases in length. Linkages between nucleobase-containing subunits can be of any type. Non-limiting examples of suitable oligomeric structures include oligo 2'-deoxyribonucleotides (i.e., DNA) and oligo ribonucleotides (i.e., RNA), locked nucleic acids (LNA) and peptide nucleic acids (PNA). A nucleobase oligomer can be enzymatically extendable or enzymatically non-extendable.

"Nucleic acid" is a nucleobase polymer having a backbone formed from nucleotides, or nucleotide analogs. "Nucleic acid" and "polynucleotide" are considered to be equivalent and interchangeable, and refer to polymers of nucleic acid bases comprising any of a group of complex compounds composed of purines, pyrimidines, carbohydrates, and phosphoric acid. Nucleic acids are commonly in the form of DNA or RNA. The term "nucleic acid" includes polynucleotides of genomic DNA or RNA, cDNA, semi-synthetic, or synthetic origin. Nucleic acids may also substitute standard nucleotide bases with nucleotide isoform analogs, including, but not limited to iso-C and iso-G bases, which may hybridize more or less permissibly than standard bases, and which will preferentially hybridize with complementary isoform analog bases. Many such isoform bases are described, for example, at www.idtdna.com. The nucleotides adenosine, cytosine, guanine and thymine are represented by their one-letter codes A, C, G, and T respectively. In representations of degenerate primers or mixture of different strands having mutations in one or several positions, the symbol R refers to either G or A, the symbol Y refers to either T/U or C, the symbol M refers to either A or C, the symbol K refers to either G or T/U, the symbol S refers to G or C, the symbol W refers to either A or T/U, the symbol B refers to "not A", the symbol D refers to "not C", the symbol H refers to "not G", the symbol V refers to "not T/U" and the symbol N refers to any nucleotide.

"Nucleoside" refers to a compound consisting of a nucleobase linked to the 1'-carbon atom of a sugar, such as ribose, arabinose, xylose, and pyranose, in the natural beta or the alpha anomeric configuration. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR2 or halogen groups, where each R is independently H, C1-C6 alkyl or C5-C1-4 aryl. Ribose examples include ribose, 2'-deoxyribose, 2',3'-dideoxyribose, 2'-haloribose, 2'-fluororibose, 2'-chlororibose, and 2'-alkylribose, e.g., 2'-O-methyl, 4'-alpha-anomeric nucleotides, 1'-alpha-anomeric nucleotides (Asseline et al., Nucl. Acids Res., 19:4067-74 [1991]), 2'-4'- and 3'-4'-linked and other "locked" or "LNA", bicyclic sugar modifications (WO 98/22489; WO 98/39352; WO 99/14226).

Sugars can include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L configurational isomer (L-form) (Beigelman, U.S. Pat. No. 6,251,666; Chu, U.S. Pat. No. 5,753,789; Shudo, EP0540742; Garbesi et al., Nucl. Acids Res., 21:4159-4165 (1993); Fujimori, J. Amer. Chem. Soc., 112:7435 (1990); Urata, (1993) Nucleic Acids Symposium Ser. No. 29:69-70). When the nucleobase is purine, e.g., A or G, the ribose sugar is attached to the N9-position of the nucleobase. When the nucleobase is pyrimidine, e.g., C, T or U, the pentose sugar is attached to the N'-position of the nucleobase.

"Nucleotide" refers to a phosphate ester of a nucleoside, as a monomer unit or within a polynucleotide polymer. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g., alpha.-thio-nucleotide 5'-triphosphates. For a review of polynucleotide and nucleic acid chemistry, see Shabarova, Z. and Bogdanov, A. Advanced Organic Chemistry of Nucleic Acids, VCH, New York, 1994.

"Polymorphic site" means a base position of a polynucleotide characterized by polymorphic variation in the type of nucleobase.

"Polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, e.g., 3'-5' and 2'-5', inverted linkages, e.g., 3'-3' and 5'-5', branched structures, or internucleotide analogs. A "polynucleotide sequence" refers to the sequence of nucleotide monomers along the polymer. "Polynucleotides" are not limited to any particular length of nucleotide sequence, as the term "polynucleotides" encompasses polymeric forms of nucleotides of any length. Polynucleotides that range in size from about 5 to about 40 monomeric units are typically referred to in the art as oligonucleotides. Polynucleotides that are several thousands or more monomeric nucleotide units in length are typically referred to as nucleic acids. Polynucleotides can be linear, branched linear, or circular molecules. Polynucleotides also have associated counter ions, such as H+, NH4+, trialkylammonium, Mg2+, Na+ and the like.

Polynucleotides that are formed by 3'-5' phosphodiester linkages are said to have 5'-ends and 3'-ends because the mononucleotides that are reacted to make the polynucleotide are joined in such a manner that the 5' phosphate of one mononucleotide pentose ring is attached to the 3' oxygen (i.e., hydroxyl) of its neighbor in one direction via the phosphodiester linkage. Thus, the 5'-end of a polynucleotide molecule has a free phosphate group or a hydroxyl at the 5' position of the pentose ring of the nucleotide, while the 3' end of the polynucleotide molecule has a free phosphate or hydroxyl group at the 3' position of the pentose ring. Within a polynucleotide molecule, a position or sequence that is oriented 5' relative to another position or sequence is said to be located "upstream," while a position that is 3' to another position is said to be "downstream." This terminology reflects the fact that polymerases proceed and extend a polynucleotide chain in a 5' to 3' fashion along the template strand.

A polynucleotide may be composed entirely of deoxyribonucleotides, entirely of ribonucleotides, or chimeric mixtures thereof. Polynucleotides may be composed of internucleotide nucleobase and sugar analogs. Unless denoted otherwise, whenever a polynucleotide sequence is represented, it will be understood that the nucleotides are in 5' to 3' orientation from left to right and that "A" denotes deoxyadenosine, "C" denotes deoxycytidine, "G" denotes deoxyguanosine, and "T" denotes thymidine.

"Polynucleotide template" means the region of a polynucleotide complementary to an oligomer, probe or primer polynucleotide. It is understood that a polynucleotide template will normally constitute a portion of a larger polynucleotide molecule, with the "template" merely referring to that portion of the polynucleotide molecule to which the oligomer, probe or primer of the present invention is complementary or to the portion of the polynucleotide molecule to be synthesized during replication. The term "template" thus refers to the region of the polynucleotide that constitutes the physical template for hybridization or replication of another complementary polynucleotide.

"Primer" means an oligonucleotide molecule that is complementary to a portion of a target sequence and, upon hybridization to the target sequence, has a free 3'-hydroxyl group available for polymerase-catalyzed covalent bonding with a 5'-triphosphate group of a deoxyribonucleoside triphosphate molecule, thereby initiating the enzymatic polymerization of nucleotides complementary to the template. Primers may include detectable labels for use in detecting the presence of the primer or primer extension products that include the primer.

"Primer extension" means the process of elongating an extendable primer that is annealed to a target in the 5'→3' direction using a template-dependent polymerase. The extension reaction uses appropriate buffers, salts, pH, temperature, and nucleotide triphosphates, including analogs and derivatives thereof, and a template-dependent polymerase. Suitable conditions for primer extension reactions are well known in the art. The template-dependent polymerase incorporates nucleotides complementary to the template strand starting at the 3'-end of an annealed primer, to generate a complementary strand.

"Probe" refers to a nucleobase oligomer that is capable of forming a duplex structure by complementary base pairing with a sequence of a target polynucleotide, and further where the duplex so formed is detected, visualized, measured and/or quantitated. In some embodiments, the probe is fixed to a solid support, such as in a column, a bead, a chip or other array format. Probes may include detectable labels for use in detecting the presence of the probe.

"Purine-like" and "Pyrimidine-like" mean carbon/nitrogen ring systems isosteric to natural purines or pyrimidines and bearing only the types of functionality found in the natural nucleobases.

"Target", as used in reference to a "target polymorphic site" and the like, refer to a specific polynucleobase sequence that is the subject of hybridization with a complementary nucleobase polymer (e.g., an oligomer). The nature of the target sequence is not limiting, and can be any nucleobase polymer of any sequence, composed of, for example, DNA, RNA, substituted variants and analogs thereof, or combinations thereof. The target can be single-stranded or double-stranded. In primer extension processes, the target polynucleotide which forms a hybridization duplex with the primer may also be referred to as a "template." A template serves as a pattern for the synthesis of a complementary polynucleotide. A target sequence for use with the present invention may be derived from any living or once living organism, including but not limited to prokaryote, eukaryote, plant, animal, and virus, as well as non-natural, synthetic and/or recombinant target sequences.

"Tm" is used in reference to the "melting temperature." The melting temperature is the temperature at which half of a population of double-stranded polynucloetide molecules or nucleobase oligomers, in homoduplexes or heteroduplexes, become dissociated into single strands. The Tm of a double-stranded nucleobase oligomeric molecule is influenced by the types of bases, the base sequence, structure of the oligomeric linkages, and the presence of non-natural features in the sequence, such as artificial linkages. Methods for calculating or experimentally determining Tm are known in the art. See, for example, Breslauer et al. Proc. Natl. Acad. Sci. USA 83: 3746-3750 (1986); Baldino et al. Methods in Enzymol. 168: 761-777 (1989); and Breslauer Methods in Enzymol. 259: 221-242 (1995).

The practice of the present invention will employ, unless otherwise indicated, conventional techniques of molecular biology, microbiology, recombinant DNA techniques, and oligonucleotide synthesis which are within the skill of the art. Such techniques are explained fully in the literature. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.), the contents of all of which are incorporated herein by reference.

Degenerate Nucleobase Oligomers

Degenerate probes have been previously used to hybridize a single nucleic acid sequence non-selectively to target sequences having polymorphic sites. Degenerate probes are created from otherwise specific sequences with nucleobase analogs acting as degenerate bases opposite polymorphic target sites. Interaction of an analog and intended target nucleobases should be non-selective and should not be markedly destabilizing relative to Watson-Crick interaction. A significant challenge in designing a degenerate base is to compensate for the different hydrogen bonding patterns presented by the standard nucleobase constituents of nucleic acids (A, C, G, and T/U). Non-selective pairing with two or more of the standard nucleobases has previously been accomplished through tautomerization (Kong et al., Synthesis of oligodeoxyribonucleotides containing degenerate bases and their use as primers in the polymerase chain reaction. Nucleic Acids Res. 20:5149-5152 (1992)), bond rotation to present different hydrogen bonding faces (Seela et al., The N8-(2'-deoxyribofuranoside) of 8-aza-7-deazaadenine: a universal nucleoside forming specific hydrogen bonds with the four canonical DNA constituents, Nucleic Acids Res. 28:3224-3232 (2000)), or by dispensing with hydrogen bonding altogether (Berger et al., Universal bases for hybridization, replication, and chain termination, Nucleic Acids Res. 28:2911-2914 (2000); Loakes et al., 5-Nitroindole as an universal base analog. Nucleic Acids Res. 22:4039-4043 (1994)).

Conformational Pairing Analysis

For purposes of designing degenerate nucleobase oligomers, it is desirable that the degenerate nucleobases pair with corresponding nucleobases based on the same types of hydrogen bonding interactions between standard nucleobases. Thus, nucleobase analogs considered here have carbon/nitrogen ring systems isosteric to natural nucleobases and bearing only the types of functionality found in the natural nucleobases. In pairs formed from such analogs, determination of the number of hydrogen bonds (H-bonds) and potential repulsive interactions in accessible pairing conformations allows prediction, to a first approximation, of the relative stability of most such pairs (;)). These analogs are referred to as "purines" or "pyrimidines" and the ring system and pattern of H-bonding functionality are denoted by the designations of Benner and coworkers (FIG. 1) (Lutz et al., Differential discrimination of DNA polymerases for variants of the non-standard nucleobase pair between xanthosine and 2,4-diaminopyrimidine, two components of an expanded genetic alphabet, Nucleic Acids Res. 24:1308-1313 (1996)). Relative stability of some purine-purine pairs is not straightforward because of accessible syn and anti purine conformations, while purine-pyrimidine and pyrimidine-pyrimidine pairs are quite tractable in such an analysis. However, pyrimidine-pyrimidine pairs in duplex DNA are usually significantly destabilizing versus purine-pyrimidine pairs and are correspondingly less useful as degenerate bases. From these considerations only purine-pyrimidine interaction was used to devise nucleobase analogs hybridizing non-selectively to relatively common purine (R) or pyrimidine (Y) polymorphic sites.

Certain analog H-bonding patterns were identified that are able to form a maximum number of H-bonds in purine-pyrimidine interaction with targets, so pairing with these targets would minimally destabilize duplex DNA. Watson-Crick pairing is the only feasible way for purine-pyrimidine pairs to form three H-bonds, so no analog can form three H-bonds in Watson-Crick pairing with two or more nucleobases. Generally slightly less stable are three energetically feasible pairing conformations within nucleic acid duplexes of purine-pyrimidine pairs joined by two H-bonds (Geyer et al., Nucleobase pairing in expanded Watson-Crick-like genetic information systems. Structure 11: 1485-1498 (2003)). These three conformations are Watson-Crick pairing of nucleobases in which at least one partner lacks a third H-bonding functional group (as in the A-T pair), "wobble" pairing (as in the G•T pair), or a conformation sometimes called "reverse wobble" pairing, that is not possible among the natural nucleobase pairs (FIG. 2).

Figure 3:
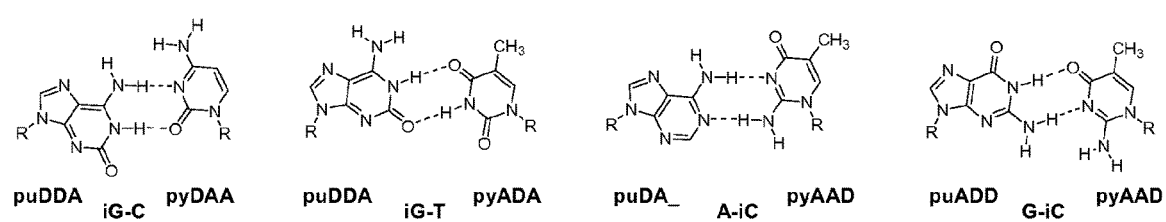
FIG. 3 shows hydrogen bond pairing for degenerate nucleobase pairs. Degenerate purines forming wobble and reverse wobble conformations associated by two hydrogen bonds opposite cytosine (pyDAA) and thymine (pyADA), respectively, are puDDA. Isoguanine is a an example of a puDDA nucleobase. Degenerate pyrimidines forming wobble and reverse wobble conformations associated by two hydrogen bonds opposite adenine (puDA_) and guanine (puADD), respectively, are pyAAD. 5-methylisocytosine is an example of a pyAAD nucleobase.

Two patterns of hydrogen bonding on a pyrimidine and one pattern on a purine can form two H-bonds in these conformations with two standard nucleobases (FIG. 3). Relative purine-pyrimidine stabilities were used to predict which of these candidates would make superior degenerate bases. pyADA analogs, including standard pyrimidine T, as a degenerate base opposite R polymorphisms have one pairing mode (Watson-Crick) that is generally more energetically favorable than the other pairing mode (wobble). Thus, pyADA is generally selective for A relative to G. In contrast, pyAAD analogs, including 5-methylisocytosine (F or iC), utilize two pairing modes of generally comparable stability in pairing with R polymorphic sites and should be non-selective. Similarly, puDDA analogs, including isoguanine (J or iG), should be non-selective among Y polymorphic positions.

One aspect of the present invention relates to a novel approach for conformational pairing of degenerate nucleobase analogs with other nucleobases. In accordance with the present invention, novel oligonucleotide molecules are prepared that comprise a degenerate nucleobase complementary to multiple nucleobase variations at a polymorphic site of a polynucleotide template and having a hydrogen bonding pattern consisting of pyAAD or puDDA. Examples of degenerate nucleobases having a hydrogen bonding pattern of pyAAD include, for example, 5-methylisocytidine, isocytidine, and 2'-deoxy analogs thereof. Examples of degenerate nucleobases having a hydrogen bonding pattern of puDDA include, for example, isoguanosine, 7-deazaisoguanosine, 7-deaza-8-azaisoguanosine, N6-(6-aminohexyl)isoguanosine, N6-(2-(1H,imidazol-4-yl)-ethyl) isoguanosine, N6-(N-(Dabcyl)-6-aminohexyl)isoguanosine, and 2'-deoxy analogs thereof. In accordance with this novel approach, pyAAD analogs, such as 5-methylisocytosine, and pyDDA analogs, such as isoguanine, were specifically identified and used as degenerate bases opposite R or Y polymorphic sites.

The usual method of addressing polymorphic sites in probe binding regions is to use a mixture of probes targeted to individual sequence motifs. The use of degenerate probes offers the advantage of reducing the number and total amount of probes required. Fewer probes simplify assay optimization and can reduce background signal, while simultaneously reducing oligonucleotide costs. These factors can be significant in technologies such as branched DNA, where numerous individual probes are currently used to target an analyte, or even in quantitative PCR targeting regions of high sequence variability. Degenerate probes could be especially useful when oligonucleotides are immobilized on a surface with limited area, such as a bead or chip. Analogs, such as J and F, can also allow targeted polymorphic sites to be near incidental sequence variation in hybridization probe melting measurements.

An additional potential use of the analogs is in PCR primers targeted to regions with polymorphisms. Isolated J and F positions in oligonucleotide templates have been demonstrated to direct incorporation of T and A nucleotides, respectively, by thermophilic Family A polymerases commonly used in PCR amplification (Ahle et al., Sequence determination of nucleic acids containing 5-methylisocytosine and isoguanine: identification and insight into polymerase replication of the non-natural nucleobases, Nucleic Acids Res. 33:3176-3184 (2005). These misincorporations are tolerated if a polymerase does not encounter frequent analog positions, suggesting degenerate primers with J and F are possible.

Nucleic acids are unique among biopolymers in that sequence variation produces virtually no change in duplex structure. Regular nucleobase pairing responsible for this characteristic extends to isosteric nucleobase analogs, and these analogs have been successfully used to directly mimic the kinds of structure observed in natural systems, such as Watson-Crick base pairing (Lutz et al., Differential discrimination of DNA polymerases for variants of the non-standard nucleobase pair between xanthosine and 2,4-diaminopyrimidine, two components of an expanded genetic alphabet, Nucleic Acids Res. 24:1308-1313 (1996)) or wobble pair formation (Strobel et al., The 2,6 diaminopurine riboside-5-methylisocytidine wobble base pair: an isoenergetic substitution for the study of G•U pairs in RNA, Biochemistry 33:13824-13835 (1994)). This regular pairing allows a simple conformational pairing analysis to yield predictions of relative pairing stability. This method of devising degenerate bases is the first example of using predictable nucleobase pairing to extrapolate a more complex pairing function. Similar conformational pairing analyses can also be used in devising degenerate nucleobases or other useful pairing schemes relevant to non-natural nucleic acid systems that can be constructed from alternative nucleobase pairs (Geyer et al., Nucleobase pairing in expanded Watson-Crick-like genetic information systems. Structure 11: 1485-1498 (2003)).

Examples of Specific Embodiments of the Invention

The present invention relates to novel nucleobase oligomers (or oligonucleotides) that hybridize to a corresponding binding region of a polynucleotide template. The nucleobase oligomers of the invention are useful for hybridization to a polynucleotide template having multiple polymorphic loci (sites where polymorphisms give rise to multiple genetic variants). When multiple polymorphic loci are present in close proximity, particularly within a region to which one wishes to have an oligonucleotide probe or primer hybridize, the presence of one polymorphic locus may complicate detection, identification or characterization of another polymorphic locus. For example, a common method of detecting a particular allele utilizes melting curve analysis to determine the particular nucleotide sequence at a specific target polymorphic locus. Melting curve analysis utilizes a hybridization probe that, typically, is exactly complementary to the nucleotide sequence of one allele at the target polymorphic locus, but differs from other known alleles at that locus. The hybridization probe thus binds to one allele with higher affinity than the other alleles, resulting in the probe dissociating from the polymorphic locus at a different, and distinctive, melting temperatures. If, however, the binding region of the polynucleotide template has other polymorphic sites, those other polymorphic sites may alter the melting curve profile and confound accurate detection and characterization of the target polymorphic locus. The materials and methods of the present invention permit accurate detection and characterization of a target polymorphic locus, even when other polymorphic loci are located in close proximity.

In one aspect, the present invention includes nucleobase oligomers comprising a base-specific nucleobase complementary to and capable of specifically hybridizing to at least one allele of a target polymorphic locus of the binding region, and a degenerate nucleobase complementary to and capable of hybridizing non-selectively to each allele of one or more non-target polymorphic locus of the binding region.

In another aspect, the present invention includes a polynucleotide duplex, comprising: a degenerate nucleobase oligomer hybridized to a corresponding binding region of a polynucleotide template; wherein the binding region of the polynucleotide template comprises a target polymorphic locus and one or more non-target polymorphic locus; and wherein the degenerate nucleobase oligomer comprises (i) a base-specific nucleobase complementary to and capable of specifically hybridizing to at least one allele of a target polymorphic locus, and (ii) a degenerate nucleobase complementary to and capable of hybridizing non-selectively to each allele of one or more non-target polymorphic locus.

In yet another aspect, the present invention includes a method for preparing a degenerate nucleobase oligomer corresponding to a binding region of a polynucleotide template, comprising: determining the nucleotide sequence of a binding region of a polynucleotide template, wherein the binding region of the polynucleotide template comprises a target polymorphic locus and one or more non-target polymorphic locus; and preparing a degenerate nucleobase oligomer comprising (i) a base-specific nucleobase complementary to and capable of specifically hybridizing to at least one allele of the target polymorphic locus, and (ii) a degenerate nucleobase complementary to and capable of hybridizing non-selectively to each allele of one or more non-target polymorphic locus.

In still another aspect, the present invention includes a method for hybridizing a degenerate nucleobase oligomer to a binding region of a polynucleotide template, comprising: determining the nucleotide sequence of a binding region of a polynucleotide template, wherein the binding region of the polynucleotide template comprises a target polymorphic locus and one or more non-target polymorphic loci; preparing a degenerate nucleobase oligomer comprising (i) a base-specific nucleobase complementary to and capable of specifically hybridizing to at least one allele of a target polymorphic locus, and (ii) a universal nucleobase complementary to and capable of hybridizing non-selectively to each allele of one or more non-target polymorphic locus; and hybridizing the degenerate nucleobase oligomer to the binding region of the polynucleotide template, under conditions wherein each degenerate nucleobase of the oligomer hybridizes non-selectively to each allele of the corresponding non-target polymorphic locus to form a duplex.

In another aspect, the present invention includes a method for amplifying a polynucleotide template having a plurality of polymorphic loci, comprising: providing a polynucleotide template having a primer binding region comprising a target polymorphic locus and one or more non-target polymorphic locus; providing a degenerate nucleobase oligomer comprising (i) a base-specific nucleobase complementary to and capable of specifically hybridizing to at least one allele of a target polymorphic locus, and (ii) a degenerate nucleobase complementary to and capable of hybridizing non-selectively to each allele of one or more non-target polymorphic locus; hybridizing the degenerate nucleobase oligomer to the primer binding region of the polynucleotide template to form a duplex, under conditions wherein each degenerate nucleobase of the oligomer hybridizes non-selectively to each allele of the corresponding non-target polymorphic locus to form a duplex; and subjecting the duplex to polymerase chain reaction under conditions sufficient to amplify the polynucleotide template.

In still another aspect, the present invention includes a method for determining the genotype of a polynucleotide template, comprising: providing a polynucleotide template having a binding region comprising a target polymorphic locus and one or more non-target polymorphic locus; providing a degenerate nucleobase oligomer comprising (i) a base-specific nucleobase complementary to and capable of hybridizing to at least one allele of the target polymorphic locus and (ii) a degenerate nucleobase complementary to and capable of hybridizing non-selectively to each allele of the non-target polymorphic loci; hybridizing the degenerate nucleobase oligomer to the binding region of the polynucleotide template to form a duplex, under conditions wherein each degenerate nucleobase of the oligomer hybridizes non-selectively to each allele of the corresponding non-target polymorphic locus; disassociating the nucleobase oligomer from the polynucleotide template under conditions sufficient to generate a melting curve profile of the duplex characteristic of the allele of the target polymorphic locus.

In other embodiments of the invention, the degenerate nucleobase of the oligomer is flanked by natural nucleobases.

In yet another embodiment of the invention, the degenerate nucleobase of the oligomer is complementary to any two purines or purine analogs.

In yet another embodiment of the invention, the degenerate nucleobase of the oligomer is complementary to any two pyrimidine or pyrimidine analogs.

In yet another embodiment, the base-specific nucleobase hybridizes selectively to each allele of the target polymorphic locus.

In a particular embodiment, the base-specific nucleobase is non-complementary to a single allele of the polymorphic locus.

In another particular embodiment, the base-specific nucleobase is complementary to a single allele of the polymorphic locus.

Degenerate Nucleobases

The present invention relates to oligonucleotide probes and primers that utilize universal or degenerate nucleobases. As used herein and in the art, the terms "universal nucleobase" and "degenerate nucleobase" refer to a base that, when incorporated into a polymeric structure in the form of a nucleobase (e.g., a nucleotide or a PNA) does not significantly discriminate between bases at a corresponding base position of a complementary polymeric structure. In principal, a universal base pairs non-selectively with all four natural nucleobases (A, C, G and T/U), although the term "universal base" is sometimes used to describe analogs that are non-selective for only a subset of the four bases. Thus, a degenerate base may base-pair with a base on a complementary polymer, but does not base-pair in a significantly different way with different bases placed in a complementary position on an opposite polynucleobase strand. Alternatively, a degenerate base may not base-pair to a significant degree with any base on a complementary polymer. Where a first nucleotide sequence hybridizes with a partially complementary second nucleotide sequence, a degenerate base included in the first nucleotide sequence is effective to reduce the Tm penalty that would otherwise result by inclusion of a mismatched nucleotide in that position of the first nucleotide sequence. A degenerate base may be effective to reduce the Tm penalty with respect to such mismatches by about 1° C., or by about 2° C., or by about 4° C., or by about 6° C., or by about 8° C., or by about 10° C., or by greater amounts. Similarly, groups or combinations of degenerate bases may be effective to reduce the Tm penalty of sequence mismatches by about 2° C., or by about 5° C., or by about 10° C., or by about 15° C., or by about 25° C., or by about 50° C., or by greater amounts. Such reductions in the Tm penalty of sequence mismatches may be the result of reduced amounts of destabilization of hybridization by about 1 kcal per mole, or by about 2 kcal per mole, or by about 5 kcal per mole, or by about 15 kcal per mole, or by about 25 kcal per mole, or by about 50 kcal per mole, or by greater amounts of reduction in the energetic penalty due to sequence mismatches. It is understood that the terms "universal nucleobase" and "degenerate base" comprise the universal or degenerate base and the backbone structure.

A degenerate base for any two purines (or purine analogs) or pyrimidines (or pyrimidine analogs) can be designed to have very similar thermodynamic association with either of the two complementary nucleobases. The degenerate base will lead to similar melting temperatures (Tms) in duplexes containing the degenerate base paired opposite either of its intended complementary nucleobases. The degenerate base may also function similarly opposite additional nucleobases, especially in the case of purine-purine pairs.

A pyrimidine or analog (py) is used opposite two purines (adenine and guanine, in the case of natural DNA) such that the pyrimidine forms a "wobble" pair with one of the purines and a "reverse wobble" pair with the other purine. Similarly, a purine or analog (pu) is used opposite two pyrimidines (cytosine and uracil or thymine) such that the pyrimidine forms two hydrogen bonds in a "wobble" pair with one of the pyrimidines and two hydrogen bonds in a "reverse wobble" pair with the other pyrimidine. The hydrogen bonding patterns of the natural purines can be denoted as puDA and puADD (FIG. 1). Using this notation the degenerate base appropriate for these purines is pyAAD (FIG. 3). One possibility of a pyAAD base is 5-methylisocytosine. The hydrogen bonding patterns of the natural pyrimidines are pyDAA and pyADA, so a degenerate base for these pyrimidines is puDDA (FIG. 3). One possibility of a puDDA base is isoguanine.

One feature of a degenerate base derived in this way is very similar association between the base and either of the intended target nucleobases. Wobble and reverse wobble pairs within a nucleic acid duplex impart similar stability to the duplex, leading to very similar Tms (Geyer, C. R., Battersby, T. R., and Benner, S. A. (2003) Nucleobase pairing in expanded Watson-Crick-like genetic information systems. Structure 11, 1485-1498). Another feature is the relative stability of the degenerate base opposite the target nucleobases. The natural wobble base pair G-T is a relatively stable mismatch (Allawi, H. T. and SantaLucia, J., Jr. (1997) Thermodynamics and NMR of internal G•T mismatches in DNA. Biochemistry 36, 10581-10594) and wobble pairs derived from unnatural analogs are similarly stable (Geyer et al.). Reverse wobble base pairs, although not found in nature, are also relatively stable mismatches (Geyer et al.).

While degenerate bases derived in this fashion ensure non-selective association opposite the two nucleobases used in the design of the degenerate base, the design does not preclude functioning as a degenerate base opposite additional nucleobases in the genetic alphabet, especially when the degenerate base is a purine or purine analog. For example, isoguanine not only imparts similar stability to a duplex opposite cytosine or thymine, it also imparts similar stability to a duplex opposite guanine in a purine-purine mismatch. Therefore, isoguanosine can function as a degenerate base opposite C, T(U), and G.

In one embodiment, for example, a universal base can pair with each of the natural bases equally well when opposite them in an oligonucleotide duplex. However, degenerate bases that are able to pair with a subset of the natural base also find use with the invention.

In one embodiment, for example, a degenerate base may be covalently attached to the 1'-carbon of a pentose sugar (e.g., ribose) backbone to make a degenerate nucleotide. In this case, polymerization of the nucleobases is by phosphodiester bonds to form either DNA or RNA.

Some degenerate bases are not naturally occurring and are predominantly hydrophobic molecules that can pack efficiently into duplex DNA (i.e., are able to form stacking interactions due to their hydrophobic nature). Degenerate bases typically refer to a nitrogen-containing aromatic heterocyclic moiety capable of participating in stable antiparallel duplex oligomer interactions in pairing with each or some subset of the naturally occurring bases.

A universal or degenerate nucleobase may or may not hydrogen bond specifically with another nucleobase. In one preferred aspect, the universal nucleobase has no preferential affinity for any particular base, but has the ability to stably base pair to any other on an antiparallel polymer of nucleobases. In other embodiments, a universal degenerate nucleobase may or may not demonstrate hydrophobic base-stacking interactions with adjacent nucleobases in a nucleobase polymer or with nucleobases in a complementary nucleobase polymer.

Thus, a universal or degenerate nucleobase may be a base that does not significantly discriminate between certain bases on a complementary polymeric structure having nucleobases, and a specificity-determining nucleobase may be a base that is capable of discriminating between bases on a complementary polymeric structure having nucleobases.

Universal base analogs are well-known in the art, and many examples of nucleobases that function as degenerate bases opposite all four natural nucleobases have been previously reported. Hypoxanthine (called inosine as the nucleoside) has long been known to pair somewhat equivalently and without severe duplex destabilization opposite the four standard nucleobases in nucleic acids (Martin et al., Nucleic Acids Res. 13, 8927-8938, 1985). Other nucleobase analogs have also been similarly employed, including 3-nitropyrrole (Nichols et al., Nature 369, 492-493, 1994), 5-nitroindole (Loakes et al., Nucleic Acids Res. 22, 4039-4043, 1994) and 8-aza-7-deazaadenine (Seela, et al., Nucleic Acids Res. 28, 3224-3232, 2000). Other degenerate analogs have been reported for pairing with a subset of the four natural nucleobases. For example, 6H,8H-3,4-Dihydropyrimido[4,5-c][1,2]oxazin-7-one and 2-amino-6-methoxyaminopurine have been designed to pair, respectively, with the natural purines and pyrimidines (Lin et al., Nucleic Acid Res. 20, 5149-5152, 1992).

Other universal base analogs are also known in the art, and include the nucleoside forms 5-nitro,1-($\beta$-D-2-deoxyribofuranosyl)indole, termed 5-nitroindole, (see Loakes and Brown, Nucleic Acids Res. 22:4039-4043 [1994]), and 1-(2'-deoxy-$\beta$-D-ribofuranosyl)-3-nitropyrrole, termed 3-nitropyrrole (see Nichols et al., Nature 396:492-493 [1994] and Bergstrom et al., J. Am. Chem. Soc. 117:1201-1209 [1995]). See also, for example, Ohtsuka et al., J. Biol. Chem. 260(5):2605-2608 (1995); Habener et al., Proc. Natl. Acad. Sci. USA 85:1735-1739 [1988]; Van Aershot et al., Nucleic Acids Res. 23:4363-4370 [1995]; Luo et al., Nucleic Acids Res. 24:3071-3078 [1996]; Amosova et al., Nucleic Acids Res. 25:1930-1934 [1997]; Berger et al., Nucleic Acids Res. 28:2911-2914 [2000]; Seela et al., Nucleic Acids Res. 28:3224-3232 [2000]; Loakes, Nucleic Acids Res. 29:2437-2447 [2000]; Harki et al., Biochemistry 41:9026-9033 [2002]; He et al., Nucleic Acids Res. 30:5485-5496 [2002]. A universal base may be capable of forming Watson-Crick type hydrogen bonding and base stacking. Other references discussing universal bases include Berger et al., Angew. Chem. Int. Ed. Engl. (2000) 39:2940-42; Wu et al., J. Am. Chem. Soc. (2000) 122:7621-32; Berger et al., Nuc. Acids Res. (2000) 28:2911-14; Smith et al., Nucleosides & Nucleotides (1998) 17:541-554; and Ogawa et al., J. Am. Chem. Soc. (2000) 122:3274-87.

A variety of universal bases are known in the art, and include, but are not limited to: azaindole (7AI); isocarbostyril (ICS); propynylisocarbostyril (PICS); 6-methyl-7-azaindole (M7AI); imidizopyridine (Impy); pyrrollpyrizine (PP); propynyl-7-azaindole (P7AI); and allenyl-7-azaindole (A7AI). N8-(7-deaza-8-aza-adenine), being a universal base, is capable of base pairing with any other nucleobase, such as for example any of: adenine, cytosine, guanine, thymine, uracil, 5-propynyl-uracil, 2-thio-5-propynyl-uracil, 5-methylcyto sine, pseudoisocyto sine, 2-thiouracil and 2-thiothymine, 2-aminopurine, N9-(2-amino-6-chloropurine), N9-(2,6-diaminopurine), hypoxanthine, N9-(7-deazaguanine) or N9-(7-deaza-8-aza-guanine) (See, eg.: Seela et al., Nucl. Acids, Res.: 28(17): 3224-3232 (2000)). Other universal bases include 5-nitroindole, 3-nitropyrrole, 6-methyl-7-azaindole, pyrrollpyrizine, imidizopyridine, isocarbostyril, propynyl-7-azaindole, propynylisocarbostyril, allenyl-7-azaindole, 8-aza-7-deaza-2'-deoxyguanosine, 8-aza-7-deaza-2'-deoxyadenosine, 2'-deoxycytidine, 2'-deoxyuridine, 2'-deoxyadeno sine, 2'-deoxyguano sine, pyrrolo [2,3-d]pyrimidine, 3-nitropyrrole, deoxyino sine (e.g., 2'-deoxyino sine), 7-deaza-2'-deoxyino sine, 2'-aza-2'-deoxyino sine, 3'-nitroazole, 4'-nitroindole, 5'-nitroindole, 6'-nitroindole, 4-nitrobenzimidazole, nitroindazole (e.g., 5'-nitroindazole), 4-aminobenzimidazole, imidazo-4,5-dicarboxamide, 3'-nitroimidazole, imidazole-4-carboxamide, 3-(4-nitroazol-1-yl)-1,2-propanediol, and 8-aza-7-deazaadenine (pyrazolo [3,4-d]pyrimidin-4-amine). In other examples, universal nucleobases may form universal nucleosides by combining 3-methyl-7-propynyl isocarbostyril, 3-methyl isocarbostyril, 5-methyl isocarbostyril, isocarbostyril, phenyl, or pyrenyl groups with a ribose or deoxyribose.

Synthesis of Oligomers

The present invention also relates to nucleobase oligomers comprising degenerate nucleobase analogs. The nucleobase oligomers of the present invention comprise nucleobases functionally joined by a suitable backbone, to generate a nucleobase oligomer. The oligomers have a 5' or 3' orientation relative to the orientation of the nucleobases and backbone in the oligomer. The oligomers of the invention may be unlabeled, labeled with one or more reporter moieties and/or comprise one or more protected or unprotected functional groups. The means by which the two oligomers are synthesized is not limiting, as various suitable chemistries and structures are know to one familiar with the art.

The oligomers of the present invention generally comprise three parts, which are the base-specific nucleobases, the universal nucleobases and, typically, a chemically reactive moiety on either the 3' terminus or 5' terminus of the oligomer. It is not intended that the polymer backbone (i.e., the structure that serves as the scaffold for the bases) be limited to any particular chemical structure. Indeed, a wide variety of acceptable polymer structures are known in the art that find use with the invention.

In one embodiment, the nucleobase oligomers use polynucleotide chemistry to form the oligomer, where the polynucleotides comprise naturally-occurring ribonucleotides, and/or 2'-deoxyribonucleotides. These structures are enzymatically extendable, and can serve as primers for the initiation of enzymatic DNA or RNA synthesis by DNA-dependent or RNA-dependent polymerases.

In other embodiments, the nucleobases used in the nucleobase oligomers are enzymatically non-extendable. That is to say, these oligomers may comprise various modified nucleotide bases, nucleotide analogs or modified chain backbones that are unable to serve as primers in the initiation of enzymatic DNA or RNA synthesis by DNA-dependent or RNA-dependent polymerases. A large number of these structures are known in the art, and are described in various sources (see, e.g., WO 95/08556 and WO 99/34014). While the nucleobase oligomer sequences of some embodiments are able to bind complementary target molecules in a sequence-specific manner, enzymatic DNA or RNA synthesis does not occur due to the non-extendable chemical structure of the nucleobase oligomer. For example, some oligomers are unable to be enzymatically extended because they lack a 3' hydroxyl group on the ribose sugar ring required for nucleotide addition.

A large number of enzymatically non-extendable nucleobase structures are known, and find use with the present invention. It is not intended that methods of the invention be limited to the use of any one particular non-extendable nucleobase structure. Generally, enzymatically non-extendable nucleobase structures that find use with the invention may show certain advantageous properties, which may include some or all of the following: 1) oligomers having defined base sequence can be readily synthesized and have some solubility in aqueous solution, 2) the resulting oligomers are able to bind complementary target sequences in a sequence-specific manner to form stable heteroduplexes, and 3) the heteroduplexes are not subject to nuclease digestion.

It is not intended that the present invention be limited to any particular non-enzymatically extendable nucleobase oligomer structure. Examples of enzymatically non-extendable nucleobases that find use with the invention include, but are not limited to, peptide nucleic acids (PNA), locked nucleic acids (LNAs; see, WO 98/22489; WO 98/39352; and WO 99/14226), 2'-O-alkyl oligonucleotides (e.g., 2'-O-methyl modified oligonucleotides; see Majlessi et al., Nucleic Acids Research, 26(9):2224-2229 [1998]), 3' modified oligodeoxyribonucleotides, N3'-P5' phosphoramidate (NP) oligomers, MGB-oligonucleotides (minor groove binder-linked oligs), phosphorothioate (PS) oligomers, C1-C4 alkylphosphonate oligomers (e.g., methyl phosphonate (MP) oligomers), phosphoramidates, β-phosphodiester oligonucleotides, and α-phosphodiester oligonucleotides.

In addition to the modification of the termini of the oligomer blocks for ligation, the oligomers can be modified and/or properly protected to thereby incorporate functional groups for labeling or for attachment to surfaces. Such functional groups can be utilized either before or after the ligation step depending upon factors such as: 1) the oligomer synthesis chemistry (e.g., harsh deprotection conditions may destroy a label), the condensation/ligation chemistry chosen (e.g., functional groups of a desired label may interfere with the condensation chemistry) and the intended use of the functional group (e.g., whether it is intended for labeling or for attachment to a solid support).

It is not intended that the bases comprising the specificity-determining nucleobase subunits be limited to the four naturally occurring bases, i.e., adenine, thymine, guanine and cytosine, or A, T, G and C, respectively. In some embodiments, non-naturally occurring bases are used in the sequence-specific nucleobase positions. The invention contemplates, for example, the use of nucleobases comprising the following non-natural bases: 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), and N9-(7-deaza-8-aza-guanine). Binding pair motifs for these bases are known in the art.

The oligomers of the present invention can be chimeric in structure, for example, where the two oligomer blocks comprise nucleobases of different chemical structure (e.g., DNA and PNA). For example, see U.S. Pat. No. 6,316,230 and WO96/40709. The present invention thus contemplates that the nucleobase oligomers of the invention include chimeric nucleobase oligomers comprises of two or more oligomer blocks having different chemical structures, e.g., one oligomer block can comprise peptide nucleic acid and another oligomer block can comprise polynucleotides. These blocks can be ligated using suitable linker chemistry to form a chimeric insulating combinatorial nucleobase oligomer. It is also contemplated that the nucleobase subunits within one oligomer block can have differing chemical structure. As with uniform oligomeric structures, the chimeric oligomers of the invention may or may not be enzymatically non-extendable.

For example, the linkage of one oligomer block having D-DNA nucleotides with another oligomer block having L-DNA molecules provides a chimeric nucleobase oligomer able to be tagged by a reporter oligomer without affecting recognition of target nucleotide sequences in a sample and with minimal non-specific binding. Since L-DNA does not hybridize with D-DNA, the L-DNA-containing portion can hybridize with a complementary L-DNA oligomer having a reporter moiety without interfering with the hybridization of the D-DNA oligomer with a target nucleotide sequence in a sample, for example. The lack of binding affinity between L-DNA and D-DNA also greatly reduces non-specific binding of reporter oligomers since the L-DNA reporter oligomers will hybridize only with L-DNA, which is not found in most biological samples. Such chimeric D-DNA-L-DNA nucleobase oligomers thus can be readily labeled in the presence of target nucleotides with labels that are highly specific for the chimeric oligomers, for example.

In another aspect, the invention contemplates nucleobase oligomers that are formed by the ligation of oligomer blocks that have different configurations. For example, in one oligomer block, the universal nucleobases can be positioned adjacent to the linker chemistry, while in other configurations, the universal nucleobases can be positioned distal to the linker chemistry, or can be interspersed between the specificity-determining nucleobases. It is contemplated that oligomer blocks with different configurations, such as these, can be ligated with each other using suitable linker chemistry to form an insulating combinatorial nucleobase oligomer of the invention. It is not intended that the present invention be limited to the use of oligomer blocks that have the same chemical structure or configuration to synthesize a nucleobase oligomer.

Labeling of Nucleobase Oligomers

Regardless of whether the nucleobase oligomers of the invention are synthesized from nucleic acids, modified nucleic acids, nucleic acid analogs (e.g., peptide nucleic acids), or any combination or variation thereof, the molecules that are used to practice of this invention can be labeled with a suitable label/reporter moiety. For example, the insulating combinatorial nucleobase oligomers and the oligomer blocks of the invention may be labeled with a label or with multiple labels selected from the group of labels consisting of dyes, fluorescent labels, luminescent labels, radioactive labels, antigens, haptens, enzymes, enzyme substrates, protecting groups, and chemically reactive groups. Other labels may also be used, in addition to, or in conjunction with, these labels.

As used herein, the term "label" in reference to nucleobase oligomers refers to any moiety that can be attached to the oligomer and: (i) provides a detectable signal, where the signal can be in the visible wavelength spectrum or any other wavelength or particle type, e.g., a radioisotope decay particle; (ii) interacts with a second label to modify the detectable signal provided by the second label, i.e., energy transfer label pairs, e.g., FRET pairs; (iii) stabilizes hybridization, i.e., duplex formation; (iv) confers a capture function, e.g., hydrophobic affinity, antibody/antigen, ionic complexation, or (v) changes a physical property, such as electrophoretic mobility, hydrophobicity, hydrophilicity, solubility, or chromatographic behavior. Labeling can be accomplished using any one of a large number of known techniques employing known labels, linkages, linking groups, reagents, reaction conditions, and analysis and purification methods. Labels include light-emitting or light-absorbing compounds which generate or quench a detectable fluorescent, chemiluminescent, or bioluminescent signal (Kricka, L. in Nonisotopic DNA Probe Techniques (1992), Academic Press, San Diego, pp. 3-28). As used herein, the terms "label" and "reporter" may in some cases be used interchangeably.

It is contemplated that the nucleobase oligomers of the invention can be labeled with any labeling moiety or technique currently known in the art for labeling nucleic acids, modified nucleic acids or nucleic acid analogs. It is not intended that the invention be limited in any way to any particular labeling method. Techniques for labeling of nucleic acids, modified nucleic acids and nucleic acid analogs are widely known in the art, and thorough discussion and detailed protocols for labeling are available from many sources. For example, see, "Non-Radioactive Labeling, A Practical Introduction," Garman, Academic Press, San Diego, Calif. (1997).

A label or reporter moiety can be linked to any position within the nucleobase oligomers. A label can reside at a terminus of the oligomer or at a position internal to the oligomer (e.g., within or attached to the nucleobases). The labeling can occur either following synthesis of the complete oligomer, or incorporated during synthesis of the oligomer.

Fluorescent reporter dyes useful for labeling biomolecules include fluoresceins (U.S. Pat. Nos. 5,188,934; 6,008,379; 6,020,481), rhodamines (U.S. Pat. Nos. 5,366,860; 5,847,162; 5,936,087; 6,051,719; 6,191,278), benzophenoxazines (U.S. Pat. No. 6,140,500), energy-transfer dye pairs of donors and acceptors (U.S. Pat. Nos. 5,863,727; 5,800,996; 5,945,526), and cyanines (Kubista, WO 97/45539), as well as any other fluorescent label capable of generating a detectable signal. Examples of fluorescein dyes include 6-carboxyfluorescein; 2',4',1,4,-tetrachlorofluorescein; and 2',4',5',7',1,4-hexachlorofluorescein (Menchen, U.S. Pat. No. 5,118,934).

As used herein in reference to a fluorescent label, "quenching" means a decrease in the fluorescence of a fluorescent label (i.e., a fluorescent reporter moiety). A donor moiety may be a fluorophore, and an acceptor moiety (a "quencher" moiety) may be fluorophore or may be a non-fluorescent moiety. In some embodiments, the decrease in fluorescence is caused by fluorescence resonance energy transfer (FRET) associated with a quencher moiety, regardless of the mechanism. Energy transfer may occur between members of a set of energy transfer labels, the set of energy transfer labels having at least one acceptor moiety and at least one donor moiety. In embodiments of the invention, a nucleobase oligomer may have at least one energy transfer set of labels. The labels of an energy transfer set may be linked to oligomer termini, or may be linked to sites within a nucleobase oligomer. Alternatively, or in addition, an acceptor moiety and a donor moiety may be coupled to different oligomers.

Another class of labels are hybridization-stabilizing moieties which serve to enhance, stabilize, or influence hybridization of duplexes, e.g., intercalators, minor-groove binders, and cross-linking functional groups (Blackburn and Gait, Eds., "DNA and RNA Structure" in Nucleic Acids in Chemistry and Biology, 2nd Edition, (1996) Oxford University Press, pp. 15-81). Yet another class of labels effect the separation or immobilization of a molecule by specific or non-specific capture, for example biotin, digoxigenin, and other haptens (Andrus, "Chemical methods for 5' non-isotopic labeling of PCR probes and primers" (1995) in PCR 2: A Practical Approach, Oxford University Press, Oxford, pp. 39-54). Suitable haptens include fluorescein, biotin, 2,4-dinitrophenyl, digoxigenin, lipopolysaccharide; apo-transferrin; ferrotransferrin; insulin; a cytokine; gp120; β-actin; leukocyte function-associated antigen 1 (LFA-1; CD11a/CD18); Mac-1 (CD11b/CD18); glycophorin; laminin; collagen; fibronectin; vitronectin; an integrin, ankyrin; fibrinogen, Factor X; inter-cellular adhesion molecule 1 (ICAM-1); inter-cellular adhesion molecule 2 (ICAM-2); spectrin, fodrin; CD4; a cytokine receptor; an insulin receptor; a transferrin receptor; Fe+++; polymyxin B; endotoxin-neutralizing protein (ENP); an antibody-specific antigen; avidin; streptavidin; and biotin. Non-radioactive labeling methods, techniques, and reagents are reviewed in: Non-Radioactive Labeling, A Practical Introduction, Garman (1997) Academic Press, San Diego. In some embodiments, the terms "label" and "reporter" are used interchangeably.

Non-limiting examples of reporter/label moieties suitable for the direct labeling of insulating combinatorial nucleobase oligomers or oligomer blocks include, but are not limited to, a quantum dot, a minor groove binder, a dextran conjugate, a branched nucleic acid detection system, a chromophore, a fluorophore, a quencher, a spin label, a radioisotope, an enzyme, a hapten, an acridinium ester and a chemiluminescent compound. Quenching moieties are also considered labels. Other suitable labeling reagents and preferred methods of label attachment would be recognized by those of ordinary skill in the art. Any examples cited herein are intended to be merely illustrative and are non-limiting.

Labels

Non-limiting examples of haptens include, but are not limited to, 5(6)-carboxyfluorescein, 2,4-dinitrophenyl, digoxigenin, and biotin.

Non-limiting examples of fluorochromes (fluorophores) include, but are not limited to, 5(6)-carboxyfluorescein (Flu), 2',4',1,4,-tetrachlorofluorescein; and 2',4',5',7',1,4-hexachlorofluoresc-ein, other fluorescein dyes (see, e.g., U.S. Pat. Nos. 5,188,934; 6,008,379; 6,020,481, incorporated herein by reference), 6-((7-amino-4-methylcoumarin-3-acetyl)amino)hexanoic acid (Cou), 5(and 6)-carboxy-X-rhodamine (Rox), other rhodamine dyes (see, e.g., U.S. Pat. Nos. 5,366,860; 5,847,162; 5,936,087; 6,051,719; 6,191,278; 6,248,884, incorporated herein by reference), benzo-phenoxazines (see, e.g., U.S. Pat. No. 6,140,500, incorporated herein by reference) Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.), other cyanine dyes (Kubista, WO 97/45539), 6-carboxy-4',5'-dichloro-2',7'-dimethoxyfluorescein (JOE), 5(6)-carboxy-tetramethyl rhodamine (Tamara), Dye 1 Dye2 or the Alexa dye series (Molecular Probes, Eugene, Oreg.).

Non-limiting examples of enzymes that can be used as labels include, but are not limited to, alkaline phosphatase (AP), horseradish peroxidase (HRP), soy bean peroxidase (SBP), ribonuclease and protease.

The nucleobase oligomers of the invention can be used in conjunction with energy transfer label sets to form probes suitable for use in energy transfer applications (e.g., FRET probes or probes suitable for use in real-time PCR analysis, i.e., TAQMAN® analysis).

A non-limiting example of a minor groove binder is CDPI3 (see, e.g., WO 01/31063).

Label Choices and Protecting Groups

It will be apparent to one of skill in the art that when oligomers or oligomer blocks are to be synthesized in accordance with this invention to thereby produce a nucleobase oligomer, the entire nature of the potentially reactive chemical groups of the oligomer should be considered for potential side or cross-reactions. Protecting groups can also be used, as appropriate, to minimize or eliminate potential side or cross-reactions. For example, in the case where oligomers are labeled prior to synthesis to form the, it is wise to consider the potential for reactivity of functional groups on the label or labels in view of the nature of the various synthetic chemistries that can be chosen.

By way of illustration, when performing ligation reactions involving an amino group, carboxylic acid group and water soluble carbodiimide, the labels (e.g., the labels of an energy transfer set) should generally be selected to avoid unprotected reactive amino and carboxylic functional groups to thereby avoid possible side/cross reactions. One of skill in the art will therefore understand how to effect optimal ligation conditions by consideration of the nature of the reactive functional groups of the component parts in view of the nature of the particular ligation chemistry chosen.

In addition to the modification of the oligomer block termini with chemically reactive groups for ligation, the oligomer blocks can be modified and/or protected to thereby incorporate functional groups for labeling or for attachment to surfaces. Such functional groups can be utilized either before or after ligation depending upon factors such as the oligomer synthesis chemistry (e.g., harsh deprotection conditions required that might destroy a label), the ligation chemistry chosen (e.g., functional groups of the desired label might interfere with the condensation chemistry) and the intended use of the functional group (e.g., whether it is intended for labeling or for attachment to a solid support).

Articles of Manufacture

The present invention provides articles of manufacture (e.g., kits) comprising at least one nucleobase oligomer of the invention. In certain embodiments, kits serve to facilitate the performance of a process, method, assay, analysis or manipulation of interest by assembling two or more components used to carry out the methods. Kits can contain any chemical reagent, enzyme, or equipment required for use of the method. In certain embodiments, kits contain components in pre-measured amounts to minimize the need for measurements by end-users. In certain embodiments, kits include instructions for performing one or more methods of the invention. In certain embodiments, the kit components are optimized to operate in conjunction with one another.

When used in kits of the invention, the nucleobase oligomer can be made sequence-specific for any given target sequence, and can be labeled or unlabeled. If the oligomer is labeled, the label chosen will be suitable for use in the intended application. The insulating combinatorial oligomer can be prepared from any suitable polynucleobase, e.g., from PNA. The oligomers of the invention can be packaged in suitable containers, such as tubes or ampules, and can be packaged in a dried (e.g., lyophilized) form, or in an aqueous form. If necessary, the articles of manufacture in the kits can be chilled or frozen during shipping and/or storage. Any article of manufacture comprising the insulating combinatorial oligomer of the invention can further include a description of the product, specifications of the product, or instructions for use of the product.

In addition, kits of the present invention can also include, for example but not limited to, apparatus and reagents for sample collection and/or purification, apparatus and reagents for product collection and/or purification, sample tubes, holders, trays, racks, dishes, plates, instructions to the kit user, solutions, buffers or other chemical reagents, suitable samples to be used for standardization, normalization, and/or control samples. Kits of the present invention can also be packaged for convenient storage and shipping, for example, in a box having a lid.

The insulating combinatorial oligomers provided in the kits may or may not be labeled. In other embodiments, the invention provides kits comprising nucleobase oligomers as well as means for labeling the oligomers. In other embodiments, the invention provides kits comprising labeled or unlabeled oligomers as well as means (e.g., apparatus and/or reagents) for the visualization or detection the oligomers.

The invention also provides kits to facilitate use of the oligomers of the invention in various methods, e.g., any method that involves sequence-specific hybridization. Materials and reagents to carry out these methods can be provided in kits to facilitate execution of the methods. A kit of the invention comprises at least one insulating combinatorial oligomer, and optionally can additionally comprise and number of additional components, including but not limited to (i) one or more buffers; (ii) one or more nucleotide triphosphates; (iii) a nucleic acid amplification master mix; (iv) one or more polymerase enzymes, or (v) reagents or equipment suitable for the isolation/purification of a nucleic acid product. In one embodiment, the kit comprises at least two oligonucleotide primers suitable for use as primers in a PCR reaction.

In some embodiments, the present invention provides kits for conducting TAQMAN.RTM. real-time PCR analysis. These kits can include, for example but not limited to, reagents for the collection of a sample, a reverse transcriptase, primer suitable for reverse transcriptase initiation and first strand cDNA synthesis, at least one suitable blocking nucleobase oligomer, primer suitable for second strand cDNA synthesis, a DNA-dependent DNA polymerase, free deoxyribonucleotide triphosphates, and reagents suitable for the isolation/purification of the cDNA molecules produced by the reaction.

In one embodiment providing kits of the invention, a single nucleobase oligomer is provided that is specific for a single target sequence. In other embodiments, multiple nucleobase oligomers specific for a plurality of targets are provided in the kit. For example, a set of two insulating combinatorial oligomers can be provided in a single kit, where the two oligomers can be used as primers in a nucleic acid amplification reaction, such as a PCR reaction. In some embodiments, kits are provided having the nucleobase oligomers of the invention affixed to a solid phase or surface. In certain embodiments, the kits of the invention may be used to sequence at least one target nucleic acid template.

In still other embodiments, the present invention provides kits for the analysis of gene expression using the oligomers of the invention. These kits can include multiple nucleobase oligomers of the invention affixed to a suitable array or chip configuration, as well as reagents required for the detection/visualization of hybridized complexes.

Labeling of Nucleobase Oligomers for Use in Energy Transfer Application (e.g. FRET or TAQMAN®)

Pairs of labels that constitute energy transfer label sets (or energy transfer label pairs) are also useful with the nucleobase oligomers of the invention in energy transfer applications (e.g., fluorescence resonance energy transfer or FRET probes or probes suitable for use in real-time PCR analysis, i.e., TAQMAM analysis). Energy transfer probe sets have found widespread and diverse uses in cellular/molecular biological studies, and protocols for their synthesis and use are widely known in the art. See, for example, WO 99/21881, WO 99/22018 and WO 99/49293.

Generally, an energy transfer pair refers to at least two labels where the emission of one label (sometimes called the "donor" or "quencher") affects the intensity of a second label (sometimes called the "acceptor"). In one embodiment, both the donor moiety(ies) and acceptor moiety(ies) are fluorophores, and the labels comprise a FRET pair. The labels of the energy transfer set can be linked to the nucleobase oligomers at the termini or elsewhere in the nucleobase oligomers (e.g., integral to the spacer moiety). In one embodiment, each of two labels of an energy transfer set can be linked at the distal-most termini of the oligomer. In one embodiment, one oligomer block comprises the donor moiety and a second oligomer block comprises the acceptor moiety.

In this application, the energy transfer set comprising at least one energy transfer donor and at least one energy transfer acceptor moiety. Often, the energy transfer set will include a single donor moiety and a single acceptor moiety, but this is not a limitation. An energy transfer set may contain more than one donor moiety and/or more than one acceptor moiety. The donor and acceptor moieties operate such that one or more acceptor moieties accepts energy transferred from the one or more donor moieties or otherwise quenches the signal from the donor moiety or moieties. In one embodiment, both the donor moiety(ies) and acceptor moiety(ies) are fluorophores, and the labels comprise a FRET pair. Although a variety of fluorophores with suitable spectral properties might operate as energy transfer acceptors, the acceptor moiety can also be a non-fluorescent quencher-type moiety.

Non-limiting examples of quenching moieties include but are not limited to diazo-containing moieties such as aryldiazo compounds, e.g., 4-((-4-(dimethylamino)phenyl)azo) benzoic acid (dabcyl), dabsyl, homologs containing one more additional diazo and/or aryl groups; e.g., Fast Black, (see, e.g., U.S. Pat. No. 6,117,986), cyanine dyes (see, e.g., U.S. Pat. No. 6,080,868) and other chromophores such as anthraquinone, malachite green, nitrothiazole, and nitroimidazole compounds.

Transfer of energy between donor and acceptor moieties may occur through any energy transfer process, such as through the collision of the closely associated moieties of an energy transfer set(s) or through a non-radiative process such as FRET. For FRET to occur, transfer of energy between donor and acceptor moieties requires that the moieties be close in proximity and that the emission spectrum of a donor(s) have substantial overlap with the absorption spectrum of the acceptor(s) (see Yaron et al., Analytical Biochemistry 95:228-235 (1979) and particularly page 232, col. 1 through page 234, col. 1). Alternatively, collision mediated (radiation free) energy transfer may occur between very closely associated donor and acceptor moieties whether or not the emission spectrum of a donor moiety(ies) has a substantial overlap with the absorption spectrum of the acceptor moiety(ies) (see Yaron et al., Analytical Biochemistry 95:228-235 (1979) and particularly page 229, col. 1 through page 232, col. 1). This process is referred to as intramolecular collision since it is believed that quenching is caused by the direct contact of the donor and acceptor moieties (see Yaron et al., supra). It is to be understood that any reference to energy transfer in the instant application encompasses all of these mechanistically-distinct phenomena. It is also to be understood that energy transfer can occur though more than one energy transfer process simultaneously and that the change in detectable signal can be a measure of the activity of two or more energy transfer processes. Accordingly, the mechanism of energy transfer is not a limitation of this invention. Indeed, an understanding of the mechanism or mechanisms by which energy transfer works is not required to make or use the invention.

Energy transfer pairs can be used to detect/monitor nucleobase hybridization between a nucleobase oligomer of the invention and a target or template polynucleotide. When used in this manner, the nucleobase oligomers can be labeled with a suitable energy transfer pair prior to use as a probe. Suitable energy transfer pairs to use in this type of application are known in the art, where such a probe is sometimes termed a "linear beacon" or a "molecular beacon" (see, e.g., WO99/21881).

The formation of a hybridization complex between a suitably labeled nucleobase oligomer and a target polynucleotide sequence can be monitored by measuring at least one physical property of at least one member of the energy transfer set that is detectably different when the hybridization complex is formed as compared with when the nucleobase oligomer exists in a non-hybridized state. This change in detectable signal results from the change in efficiency of energy transfer between donor and acceptor moieties caused by hybridization of the oligomer to the target sequence.

For example, the means of detection can involve measuring fluorescence of a donor or acceptor fluorophore of an energy transfer set. In one embodiment, the energy transfer set comprises at least one donor fluorophore and at least one acceptor (fluorescent or non-fluorescent) quencher such that the measure of fluorescence of the donor fluorophore can be used to detect, identify or quantitate hybridization of the insulating combinatorial nucleobase oligomer to the target sequence. For example, there may be a measurable increase in fluorescence of the donor fluorophore upon the hybridization of the combination oligomer to a target sequence.

In another embodiment, the labels of the energy transfer pair reside on different nucleobase oligomers of the present invention, where one oligomer is labeled solely with a quencher moiety, and one oligomer is labeled solely with an acceptor moiety, and further where the oligomers have a domain of overlapping nucleobase complementarity and one oligomer is further specific for a target that is not the remaining oligomer. This type of label system has various uses, and is known in the art (see, e.g., WO99/49293). This labeling technique can be used in conjunction with the novel nucleobase oligomers of the present invention.

In this system, when a complex comprising the oligomer, quencher and target is formed, at least one donor moiety on the target is brought within sufficient proximity to at least one acceptor moiety on a second nucleobase oligomer bound to a second target. Since the donor and acceptor moieties of the set are in close proximity, transfer of energy occurs between moieties of the energy transfer set. However, when one of the detection complexes dissociates, as for example when a polymerase copies one of the strands of the detection complex, the donor and acceptor moieties no longer interact sufficiently to cause substantial transfer of energy from the donor and acceptor moieties of the energy transfer set and there is a correlating change in detectable signal from the donor and/or acceptor moieties of the energy transfer set. Consequently, the formation or dissociation of a complex comprising the nucleobase oligomer can be determined by measuring at least one physical property of at least one member of the energy transfer set that is detectably different when the complex is formed as compared with when the component the labeled nucleobase oligomers exist independently and are unassociated.

Applications and Methods of Use

The compositions and methods of the present invention finds use in a variety of applications. Indeed, the nucleobase oligomers of the present invention find use in any application where nucleobase oligomers are used in a hybridization protocol (i.e., as a probe or a primer). For example, the compositions and methods of the invention find use in the analysis of gene expression. It is not intended that the invention find use in only the few applications discussed herein, as one familiar with the art will immediately recognize a variety of uses for the oligomers of the invention. The uses cited herein are intended to be exemplary and not limiting, and such examples are not exhaustive. It is understood that use of the invention is not limited to any particular application cited herein, as the invention finds use with any protocol that incorporates oligomeric nucleobase sequences as probes or primers.

When used as probes or primers, it is a requirement that the nucleobase oligomers hybridize to a target sequence with sequence specificity. Thus, when used as a probe, there are no additional limitations on specific features of the insulating combinatorial nucleobase oligomer. However, when used as a primer, it is a requirement that the nucleobase oligomer be extendable by at least one polymerase enzyme.

Nucleobase Oligomers as Indicators of Hybridization

In one embodiment, the invention provides compositions and methods for detecting the presence of a target nucleobase sequence in a sample using a suitably labeled nucleobase oligomer of the invention.

The nucleobase oligomer may comprise an energy transfer set of labels (e.g., a FRET-pair of labels) as known in the art, such that at least one acceptor moiety of the energy transfer set is linked to the oligomer blocks while at least one donor moiety is linked to another oligomer, wherein labels are linked to the nucleobase oligomer at positions that facilitate a change in detectable signal of at least one of the labels when the nucleobase oligomer is sequence specifically hybridized to a target. Methods for the synthesis and use of FRET-type probes to indicate hybridization to a target sequence are known in the art. See, e.g., WO 99/21881, WO 99/22018 and WO 99/49293.

Real-Time Monitoring of PCR Products

The general application of energy transfer (e.g., FRET) labels in conjunction with the nucleobase oligomers of the invention are discussed above. Another application of energy transfer labeling is the synthesis of probes suitable for real-time monitoring of the accumulation of PCR products, i.e., TAQMAN®analysis.

The oligomers of the invention find use FRET-type probes in real-time quantitative PCR analysis. Real-time PCR analysis refers to the monitoring of accumulating PCR products (also known as a fluorogenic 5' nuclease assay, i.e., TAQMAN analysis. Methods for the synthesis and use of TAQMAN probes are well known in the art. See, for example, Holland et al., Proc. Natl. Acad. Sci. USA 88:7276-7280 [1991] and Heid et al., Genome Research 6:986-994 [1996]).

In general, the TAQMAN PCR procedure uses two oligonucleotide primers to generate an amplicon from a template typical of a PCR reaction. A third non-priming nucleobase oligomer (not necessarily a nucleotide oligomer) is also included in the reaction (the TAQMAN probe). This probe has a structure that is non-extendible by Taq DNA polymerase enzyme, and is designed to hybridize to nucleotide sequence located between the two PCR primers. The TAQMAN probe is labeled with a reporter fluorescent dye and a quencher fluorescent dye on opposite termini. The laser-induced emission from the reporter dye is quenched by the quenching dye when the two dyes are located close together, as they are when the probe is annealed to the PCR amplicon.

The TAQMAN PCR reaction uses a thermostable DNA-dependent DNA polymerase (e.g., Taq DNA polymerase) that retains 5'-3' nuclease activity despite exposure to elevated temperatures. During the PCR amplification reaction, the Taq DNA polymerase cleaves the labeled probe that is hybridized to the amplicon. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data, such that the amount of released fluorescent reporter dye is directly proportional to the amount of amplicon product.

TAQMAN assay data are expressed as the threshold cycle (CT), which is the minimal number of PCR cycles required to achieve a statistically significant detectable level of fluorescence from the reporter dye. As discussed above, fluorescence values are recorded during every PCR cycle and represent the amount of product amplified to that point in the amplification reaction.

TAQMAN RT-PCR can be performed using commercially available equipment, such as, for example, ABI PRISM® 7700 Sequence Detection System (Applied Biosystems, Foster City, Calif.), or Lightcycler (Roche Molecular Biochemicals, Mannheim, Germany). The system consists of a thermocycler, laser, charge-coupled device (CCD), camera and computer. The ABI PRISM 7700 Sequence Detection System amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

Analysis of Gene Expression

The nucleobase oligomers provided by the present invention find use in hybridization assays, e.g., in the analysis of gene expression. The insulating combinatorial oligomers of the invention are used as probes in two general capacities. First the oligomers of the invention can be labeled and used to detect a target polynucleotide. Second, the oligomers of the invention can be immobilized to a solid phase and used in an array or chip type gene expression analysis system. It is not intended that the oligomers of the present invention be limited to use in any particular hybridization format, protocol or conditions, as one familiar with the art is familiar with a variety of hybridization protocols, and recognizes well the advantages of the present invention as they apply to many hybridization formats.

In the first aspect, the oligomer of the invention is labeled prior to hybridization and use as a probe. It is not intended that the present invention place any restriction on how the labeled probe is used. As used herein, the term "label" refers to any moiety that allows isolation, cloning, detection, visualization, or quantitation of a target nucleotide sequence. The label that is covalently attached to an oligomer may be detectable by itself (e.g., fluorescein or a radioisotope), or conversely, may not be directly visualized until interaction with a secondary reagent (e.g., a biotin/strepavidin coupled dye, or a conjugated enzyme that requires the presence of a chromogenic substrate). The labeled oligomer when in a complex (e.g., a duplex) with a target sequence can be detected using a suitable method, for example but not limited to radiometric detection, calorimetric determinations, fluorescence, chemiluminescence, bioluminescence and enzyme-coupled assays. Numerous oligomer labeling/detection techniques are widely known in the art, all of which find use with the present invention. It is not intended that the present invention be limited to any particular labeling method.

In the second aspect, the hybridization reactions take place in high throughput formats, as known in the art. Generally, the high throughput hybridization formats use a probe (i.e., an oligomer of the invention) that is affixed to a solid support. The solid support can be any composition and configuration, and includes organic and inorganic supports, and can comprise beads, spheres, particles, granules, planar or non-planar surfaces, and/or in the form of wells, dishes, plates, slides, wafers or any other kind of support. In some embodiments, the structure and configuration of the solid support is designed to facilitate robotic automation technology. The steps of detecting, measuring and/or quantitating can also be done using automation technology.

In some embodiments, the hybridization format is an "array", "microarray", "chip" or "biochip" as widely known in the art (see, e.g., Ausubel et al. (eds.), Current Protocols in Molecular Biology, Chapter 22, "Nucleic Acid Arrays," John Wiley & Sons, Inc., New York [1994]; and M. Schena, (ed.), Microarray Biochip Technology, BioTechnique Books, Eaton Publishing, Natick, Mass. [2000]). In general, array formats facilitate automated analysis of large numbers of samples and/or have a large number of addressable locations, so that patterns of gene expression for a very large number of genes can be studied very rapidly. The oligomers of the invention, when used as probes, find use with array formats, and it is not intended that the oligomer probes of the present invention be limited to use in any particular array or hybridization format.

The use of polynucleotide samples in hybridization assays typically necessitate the labeling of the polynucleotide pool prior to hybridization, so that an interaction between the immobilized probe and the target can be detected. A variety of polynucleotide labeling techniques are known in the art, and it is not intended that the present invention be limited to any particular polynucleotide labeling method. The labeled polynucleotide sample permits the detection of those species that are in a duplex with a probe affixed to a solid support, such as in a microarray. A labeled polynucleotide in a duplex with the affixed probe can be detected using a suitable detection method.

In one embodiment of the invention, the labeling of the polynucleotide pool (comprising either RNA or DNA molecules) is accomplished by incorporating a suitable label into the nascent polynucleotide molecules at the time of synthesis. For example, dye-coupled UTP can be incorporated into a nascent RNA chain. In an alternative embodiment, the labeling of the polynucleotide pool is accomplished after the polynucleotide pool is synthesized. In these embodiments, the RNA or DNA molecules are labeled using a suitable label that is coupled (i.e., conjugated or otherwise covalently attached) to the polynucleotides after chain synthesis.

In still other embodiments, an unlabeled pool of polynucleotides in a sample can be used directly in hybridization or gene expression analysis using methods that do not required a labeling step. For example, duplex formation with an affixed probe can be detected using surface plasmon resonance (SPR). See, e.g., SPREETA™ SPR biosensor (Texas Instruments, Dallas, Tex.), and BIACORE 2000 (BIACORE®, Uppsala, Sweden). Resonant light scattering methods can also be used to detect duplex formation in a hybridization analysis using probes that have not been otherwise labeled (Lu et al., Sensors 1:148-160 [2001]).

It is not intended that the present invention be limited to any particular labeling, probing, or hybridization method. One skilled in the art is familiar with a wide variety of such protocols and reagents, all of which find use with the insulating combinatorial oligomers of present invention.

Use in Hybridization Reactions

The nucleobase oligomers of the invention find use in any method involving hybridization, i.e., the forming of a complex between two complementary nucleobase sequences. The complementarity need not be 100%, as effective hybridizations can occur when there is less than 100% complementarity.

The potential uses of the nucleobase oligomers of the invention are not in any way limited. Thus, one familiar with the art recognizes that the specific conditions to be used in hybridization reactions as practiced using compositions of the invention are similarly unlimited, and are dependent on the particular application and the primary sequence of the oligomers used. A wide variety of sources are available that describe hybridization conditions for particular application; see, e.g., Ausubel et al. (eds.), Current Protocols in Molecular Biology, Chapter 22, "Nucleic Acid Arrays," John Wiley & Sons, Inc., New York [1994]; and M. Schena, (ed.), Microarray Biochip Technology, BioTechnique Books, Eaton Publishing, Natick, Mass. [2000].

One of ordinary skill in the art appreciates that the stringency of a particular hybridization reaction is dependent on many variables. Although the art refers to "low stringency" or "high stringency," defining strict conditions of low or high stringency that universally apply to any and all hybridization reactions is impractical if not impossible.

A more useful definition of "stringency" for use in a particular hybridization reaction is to define a given set of hybridization conditions as more or less stringent than a second set of hybridization conditions in the same experimental system. One familiar with the art will know that a variety of factors determine stringency, including but not limited to salt concentration (i.e., ionic strength), hybridization temperature, detergent concentration, pH, the presence/concentration of chemical denaturants (e.g., formamide), and the presence/concentration of chaotropic agents (e.g., urea). Optimal stringency for a particular oligomer is often found by the well-known technique of fixing several of the aforementioned stringency factors and then determining the effect of varying a single stringency factor. Generally, these same stringency factors apply in controlling hybridization stringency for any nucleobase structure. One exception is the use of PNA oligomeric structures in hybridization reactions with nucleic acids, as PNA hybridization stability is fairly independent of ionic strength. Optimal or suitable stringency for an assay may be experimentally determined by examination of each stringency factor until the desired degree of discrimination is achieved.

Immobilization on a Solid Support (e.g. Arrays)

In one aspect, the invention pertains to compositions and methods for making and using nucleobase oligomers that are affixed to a solid support. A wide variety of solid supports find use with the invention, and it is not intended that the invention be limited to the use of any particular type of solid support. Similarly, it is not intended that the manner in which the nucleobase oligomers are affixed to the solid support be limited in any way.

In one embodiment, the support-bound nucleobase oligomers form an array (e.g., a chip) of oligomers. Detailed methods for making and using arrays comprising polymeric nucleobase structures (e.g., nucleic acid, modified nucleic acids, nucleic acid analogs, or chimeric structures) are well-known in the art and are described in many sources. See, e.g., Ausubel et al. (eds.), Current Protocols in Molecular Biology, Chapter 22, "Nucleic Acid Arrays," John Wiley & Sons, Inc., New York [1994]; and M. Schena, (ed.), Microarray Biochip Technology, BioTechnique Books, Eaton Publishing, Natick, Mass. [2000]. Any methods for the synthesis and use of nucleic acids, modified nucleic acids and nucleic acid analogs with solid supports, and more specifically arrays, are applicable for use with the present invention.

Because the location and sequence of each support bound oligomer is known, arrays can be used to simultaneously detect, identify and/or quantitate the presence or amount of one or more target sequences in a sample. For example, a target sequence can be captured by the complementary nucleobase oligomer on the array surface and then the complex containing the target sequence can be detected. Since the sequence of the nucleobase oligomer is known at each location on the surface of the array, the sequence of target sequence(s) can be directly detected, identified and/or quantitated by determining the location of a detectable signal generated on the array. Thus, arrays are useful in diagnostic applications or in screening compounds, e.g., during development of therapeutic compounds.

In one embodiment, the nucleobase oligomers can be immobilized to a surface using the well known process of UV-crosslinking.

In another embodiment, the oligomers can be synthesized on the surface in a manner suitable for deprotection but not cleavage from the synthesis support (see, e.g., Weiler et al., Hybridization based DNA screening on peptide nucleic acid (PNA) oligomer arrays," Nucl. Acids Res., 25(14):2792-2799 (1997)). In still another embodiment, one or more nucleobase oligomers can be covalently linked to a surface by the reaction of a suitable functional group on the oligomer with a functional group of the surface (see, e.g., Geiger et al., PNA Array technology in molecular diagnostics, Nucleosides & Nucleotides 17(9-11):1717-1724

(1998)). This method is advantageous since the oligomers immobilized on the surface can be highly purified and attached using a defined chemistry, thereby possibly minimizing or eliminating non-specific interactions.

Methods for the chemical attachment of nucleobase oligomers to solid support surfaces can involve the reaction of a nucleophilic group, (e.g., an amine or thiol) of the oligomer to be immobilized, with an electrophilic group on the solid support surface. Alternatively, the nucleophile can be present on the support and the electrophile (e.g., activated carboxylic acid) can be present on the oligomer. In one embodiment, in the case where the oligomer comprise PNA, the PNA used may or may not require modification prior to the immobilization reaction because PNA possesses an amino terminus in its structure.

Conditions suitable for the immobilization of a nucleobase oligomer to a surface are widely known in the art. The immobilization reaction to a solid support is analogous to a labeling reaction, where the label is substituted with the surface to which the polymer is to be linked. It is not intended that the invention be limited to any particular immobilization chemistry or method.

Numerous types of solid supports derivatized with amino groups, carboxylic acid groups, isocyantes, isothiocyanates and malimide groups are commercially available. Non-limiting examples of suitable solid supports include chips of any type (e.g., arrays), membranes, glass, controlled pore glass, polystyrene particles (beads), silica and gold nanoparticles. All of the above recited methods of immobilization are not intended to be limiting in any way but are merely provided by way of illustration.

Detection/Identification of Biological Organisms

The nucleobase oligomers of the invention find use in the detection, identification and/or enumeration of biological organisms, and especially, pathogens. Such organisms can include viruses, bacteria and eucarya in food, beverages, water, pharmaceutical products, personal care products, dairy products or in samples of plant, animal, human or environmental origin. The nucleobase oligomers find use in the analysis of raw materials, equipment, products or processes used to manufacture or store food, beverages, water, pharmaceutical products, personal care products dairy products or environmental samples. Additionally, the nucleobase oligomers find use in the detection of pathogens (e.g., various bacteria, viruses and eucarya) in clinical specimens, equipment, fixtures or products used to treat humans or animals as well as in clinical samples and clinical environments. For example, the analysis for microorganisms of interest can be performed using FISH or multiplex FISH using probes generated by the invention described herein (See: BP U.S. application Ser. Nos. 09/335,629 and 09/368, 089).

The compositions, methods, kits, libraries and arrays of this invention are particularly useful in areas such as expression analysis, single nucleotide polymorphism (SNP) analysis, genetic analysis of humans, animals, fungi, yeast, viruses, and plants (including genetically modified organisms), therapy monitoring, pharmacogenomics, pharmacogenetics, epigenomics, and high throughput screening operations.

Multiplex Analysis

In certain embodiments, the invention provides nucleobase oligomers for use in multiplex hybridization assays. In a multiplex assay, numerous conditions of interest are simultaneously or sequentially examined. Multiplex analysis relies on the ability to sort sample components or the data associated therewith, during or after the assay is completed. In performing a multiplex assay, one or more distinct independently detectable moieties can be used to label two or more different nucleobase oligomers that are to be used simultaneously in an assay. As used herein, "independently detectable" means that it is possible to determine one label independently of, and in the presence of, at least one other additional label. The ability to differentiate between and/or quantitate each of the independently detectable moieties provides the means to multiplex a hybridization assay because the data correlates with the hybridization of each distinct, independently labeled nucleobase oligomer to a particular target sequence sought to be detected in the sample. Consequently, the multiplex assays of this invention can, for example, be used to simultaneously or sequentially detect the presence, absence, number, position or identity of two or more target sequences in the same sample in the same assay.

Blocking Probes

The nucleobase oligomers of the invention can also be used as blocking probes to suppress the binding of a second nucleobase sequence to a non-target sequence. In some embodiments, the second nucleobase oligomer is labeled. Preferred blocking probes are PNA probes (see, e.g., Coull et al., U.S. Pat. No. 6,110,676, herein incorporated by reference). Although these molecules are referred to as "probes" in the art, this is somewhat of a misnomer, as the nucleobase oligomer is not labeled nor otherwise detected.

Typically, blocking probes are closely related to the probing nucleobase sequence and preferably they comprise one or more single point mutations as compared with the target sequence sought to be detected in the assay. It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence, although an understanding of the mechanism is not required to make or use the invention. Thus, nucleobase oligomers of the invention find use as blocking probes to suppress the binding of a second nucleobase oligomer to a non-target sequence that might be present in an assay and thereby interfere with the performance of the assay (see, Fiandaca et al., "PNA Blocker Probes Enhance Specificity In Probe Assays", Peptide Nucleic Acids: Protocols and Applications, pp. 129-141, Horizon Scientific Press, Wymondham, UK, 1999). The nucleobase oligomers of the invention also find use as the second (typically labeled) nucleobase molecule used in these protocols. The use of nucleobase oligomers of the invention as blocking probes extends more generally to use of the oligomers of the invention as any type of specific or non-specific nucleobase competitor in a hybridization reaction.

Polymerase Priming

The nucleobase oligomers of the invention also find use in any application using primer extension, i.e., any reaction where an oligomer acts as a primer for template-dependent ribonucleotide (RNA) or deoxyribonucleotide (DNA) elongation by a polymerase enzyme. When the insulating combinatorial nucleobase oligomers are used as primers, they are required to have a structure that permits enzymatic elongation. This will typically require the presence of a minimum number of ribonucleotide or deoxyribonucleotide-containing subunits in the nucleobase oligomers in order to serve as a polymerase primer. In one embodiment, when the nucleobase oligomer is used as a primer, the oligomer is chimeric, such that the oligomer comprises nucleotides as well as other types of nucleobase structures, including for example, PNA.

It is noted that in one aspect, the expression "primer extension" has a specific meaning in reference to a molecular genetic technique for mapping a transcription start site. However, as used herein, the expression is used in its most general sense to describe any template-directed, primer-initiated polymerase reaction.

The art knows well the wide variety of applications utilizing primer extension reactions in experimental or diagnostic methodologies. Is not intended that the invention be limited in any way to the use of nucleobase oligomers in any particular type of primer extension reactions. Various primer extension reactions are widely used in modern molecular biology techniques. For example, Sanger nucleic acid sequencing utilizes a nucleobase oligomer primer annealed to a template, deoxyribonucleotide triphosphates (dNTPs), polymerase, and four dideoxynucleotide terminators that are combined in a reaction (the four terminators are either added to separate reactions or together in one reaction), and the reaction mixture is incubated under appropriate conditions to achieve primer extension.

In one aspect, the primer extension reaction is a polymerase chain reaction (PCR). The art knows well the protocols and diversity of applications that use PCR-based techniques. See, e.g., Mullis et al. (1986) Cold Spring Harbor Symposia on Quantitative Biology 51:263; Eckert et al. (1990) Nucl. Acids Res. 18:3739, Dieffenbach et al. (1995) PCR Primer: a laboratory manual, CSHL Press, Cold Springs Harbor, USA. Generally, a PCR reaction includes at least one template, at least one primer, at least one polymerase, and extendable nucleotides. At least one of the primers in the PCR reaction can be a nucleobase oligomer of the invention. The PCR reaction is subjected to temperature cycles that result in repeated annealing, primer extension and template dissociation in the reaction mix. This generates a primer extension product (or amplicon) complementary to at least a portion of the target template.

Analysis of microsatellites, including Variable Number of Tandem Repeats (VNTRs) and Short Tandem Repeats (STRs), is another widely used method employing primer extension reactions. STRs are sequences of two to seven nucleotides that are tandemly repeated at one or more locations in the genome. The number of tandem repeats varies from individual to individual. For certain genetic analysis techniques, STRs are amplified by PCR using specific primers flanking the repeat region and the number of repeats is determined. In certain techniques, the determination is made using size differentiation, e.g., by electrophoresis, mass spectroscopy, or chromatography.

Uses of Oligomers Comprising Universal Nucleobases

It is contemplated that the nucleobase oligomers of the present invention may also be used in the synthesis of oligomer blocks, as described in US 2005/0053979, which oligomer blocks may also find use in various applications. For example, an oligomer block comprising at least one universal nucleobase can be covalently attached (i.e., via a linker) to a solid phase via the chemically reactive moiety on the oligomer block and used as an affinity ligand for the isolation and/or purification of various molecules that bind to a particular nucleobase sequence. In one aspect, the solid phase can be, for example, a bead such as a SEPHAROSE® bead, and the bead can be immobilized in a chromatography column.

In one aspect, the molecule that binds to the nucleobases of the affixed oligomer block is another polynucleobase molecule that binds by the rules of base-pairing interactions. A nucleic acid (or other nucleobase-containing structure) can be isolated/purified following the formation of a hybridization complex between the nucleobases of the oligomer block that has been attached to a solid phase and a nucleobase target. This technique can find use in the analysis of fragmented or digested DNA following enzymatic degradation, for example, or in the analysis of DNA oligomers produced by expression or in other ways.

In another aspect, the oligomer block that is affixed to a solid phase can be used to isolate/purify proteins that bind to the nucleobases of the oligomer block in a sequence-specific manner. In this case, the nucleobases of the oligomer block can prepared in a single-stranded or double-stranded configuration for the isolation/purification of single-stranded binding proteins or double-stranded binding proteins.

Genomic Analysis

Nucleobase oligomers blocks may also be used in genomic analysis. For example, a target sample of genomic material may be contacted with a probe comprising a nucleobase oligomer in order to determine whether hybridization occurs. Hybridization between the probe and the target indicates the presence in the target of nucleobase sequence complementary to that of the probe.

In preferred embodiments of the invention, a target sample of genomic material may be contacted with a plurality of probes comprising nucleobase oligomers. Hybridization between one or more of the probes and the target indicates the presence in the target of nucleobase sequence complementary to that of the hybridizing probe sequence(s). Such hybridization may be detected by detecting fluorescence from fluorescent labels attached to the probes; by quenching of fluorescence from fluorescent labels attached to the probes; by anti-body binding to antigens on the probes; by detection of radioactivity emitted by radioactive labeled probes; or by other labeling and detection methods.

Gene Expression Analysis

Gene expression may be analyzed by detection of target gene or other nucleobase sequences in a sample indicative of gene expression, such as a cDNA derived from mRNA obtained from a cell of interest. For example, a cDNA library derived from a cell of interest may be contacted with a plurality of probes comprising the nucleobase oligomers of the present invention in order to detect the presence of nucleobase sequences complementary to those of the nucleobase oligomers. Such analysis may be used to determine the expression of particular nucleobase sequences and so be indicative of the expression of genes including such nucleobase sequences.

Such gene expression analysis may be performed on similar cells under different conditions or from cells during different parts of the cell cycle (see, for example, DeRisi et al., Science 278:680-686 (1997)). Comparison of the results of such gene expression analysis may be used to determine what gene activity is altered under the different conditions or during the different parts of the cell cycle. Similarly, comparison between normal cells and cancerous cells may indicate differences in gene expression between the normal and the cancerous conditions. Thus, for example, where cDNAs are obtained from normal and cancerous cells, comparison of the hybridization between such cDNAs and with nucleobase oligomers having features of the invention may be used to determine differences in gene expression between normal and cancerous cells.

EXAMPLES

Example 1

Utility of puDDA and pyAAD Nucleobases Opposite Degenerate Sites

The reagents 5-methylisocytosine (F) and isoguanine (J) were used in experiments for thermally denaturing a dye-labeled oligodeoxyribonucleotide duplex with a single variable position containing A, C, G, T, F, or J. These experiments were used to characterize probe hybridization when F or J was paired opposite the other nucleobases. Thermal denaturation experiments yielded comparable melting temperatures (Tms) for duplexes with F opposite A or G, as well as J opposite C or T. The mean Tm of these 15 mer duplexes was only 2.9° C. lower than the mean Tm observed for the two duplexes with A opposite T at the variable duplex position.

The utility of puDDA (F) and pyAAD (J) nucleobases opposite degenerate sites was demonstrated in melting point experiments using a 15 mer oligodeoxynucleotide duplex comprising the following two sequences:

```
5'-FAM-CAGTAGGN₁TCTCCCG-BHQ-3'      (SEQ ID NO: 1)

3'-GTCATCCN₂AGAGGGC-5'              (SEQ ID NO: 2)
```

One of the oligonucleotides of each duplex was labeled with a fluorophore (FAM) and quencher (BHQ) to allow fluorescence monitoring of duplex association.

Melting Temperature Oligodeoxyribonucleotides. Oligodeoxyribonucleotides were synthesized on a 394 DNA synthesizer (Applied Biosystems) and purified by reversed phase HPLC using the Wave system (Transgenomic). ODN mass was verified as within 0.5% of the expected mass by MALDI-TOF mass spectrometry using a Voyager-DE (Applied Biosystems). ODN purity was >93% by electrophoresis in a polyacrylamide-filled capillary on a $^{3D}$CE instrument (Agilent).

Melting Temperature Determinations. Duplexes were made at 6.25 µM stock in 10 mM Tris, 0.1 mM EDTA, pH 8.5. For each replicate in denaturation experiments a duplex was diluted to 125 nM in GeneAmp PCR buffer II (Applied Biosystems) containing 5 mM MgCl$_2$. An aliquot (20 µL) of each sample was added to a capillary and denatured at 95° C. for 10 s and then relative FAM fluorescence was continuously acquired while cooling −0.1° C./s to 37° C. on a LightCycler instrument (Roche). The fluorescence data from denaturation experiments were fitted using cubic smoothing splines. $T_m$s were determined as the maximum of the first derivative of the fitted curve. $T_m$s for all possible duplex permutations were measured once and $T_m$s for duplexes of primary interest were then examined in two additional replicates.

$T_m$s ranging from 41.6° C. for C-C to 61.2° C. for F-J (Table 1) were determined as the maximum of the first derivative of the melting curve for all permutations of F, J, and the standard nucleobases. Two additional replicates were measured for 24 pairings of primary interest, which include standard nucleobase purine-pyrimidine pairs and all standard nucleobases opposite J or F (Table 2).

TABLE 1

$T_m$s for all possible duplexes $N_1$-$N_2$

| $N_1$-$N_2$ | $T_m$ (° C.) |
|---|---|
| F-J | 61.2 |
| J-F | 60.0 |
| C-G | 59.9 |
| F-G | 57.0 |
| G-C | 56.7 |
| A-T | 56.4 |
| T-A | 56.3 |
| T-J | 54.8 |
| J-T | 53.8 |
| J-G | 53.3 |
| G-F | 52.3 |
| J-C | 52.0 |
| A-G | 51.8 |
| C-J | 51.7 |
| F-A | 51.5 |
| G-J | 51.5 |
| A-F | 50.8 |
| T-G | 50.7 |
| G-G | 50.6 |
| G-T | 48.9 |
| G-A | 48.5 |
| J-J | 48.0 |
| T-T | 46.4 |
| F-C | 45.9 |
| A-A | 45.8 |
| J-A | 45.7 |
| C-F | 45.7 |
| C-A | 45.2 |
| A-J | 45.0 |
| C-T | 43.9 |
| F-T | 43.8 |
| A-C | 43.8 |
| F-F | 43.7 |
| T-C | 43.5 |
| T-F | 43.3 |
| C-C | 41.6 |

TABLE 2

Mean $T_m$s (n = 3) of selected duplexes $N_1$-$N_2$

| $N_1$-$N_2$ | Mean $T_m$ (° C.) | Std Dev |
|---|---|---|
| C-G | 59.9 | 0.1 |
| F-G | 57.2 | 0.3 |
| G-C | 56.9 | 0.2 |
| A-T | 56.4 | 0.0 |
| T-A | 56.3 | 0.2 |
| T-J | 54.7 | 0.1 |
| J-T | 53.8 | 0.2 |
| J-G | 53.3 | 0.2 |
| G-F | 52.4 | 0.1 |
| J-C | 52.3 | 0.3 |
| C-J | 52.0 | 0.3 |
| F-A | 51.8 | 0.3 |
| G-J | 51.6 | 0.1 |
| A-F | 51.1 | 0.3 |
| T-G | 50.8 | 0.1 |
| G-T | 49.0 | 0.1 |
| F-C | 46.0 | 0.1 |
| J-A | 45.9 | 0.2 |
| C-F | 45.9 | 0.2 |
| C-A | 45.3 | 0.2 |
| A-J | 45.1 | 0.1 |
| A-C | 43.9 | 0.1 |
| F-T | 43.8 | 0.1 |
| T-F | 43.3 | 0.1 |

Duplexes with F opposite purines A or G were relatively high melting, with Tms at least as high as those observed for the two duplexes containing G•T wobbles, but somewhat lower than the duplexes with only Watson-Crick matched pairs. Tms for duplexes with F opposite the standard nucleobases were compared to Tms of duplexes with standard purine-pyrimidine pairings (FIG. 4b). Tms of duplexes with F opposite standard purines were more tightly clustered than Tms of either C or T opposite standard purines. Tms for duplexes with F opposite standard pyrimidines C or T were significantly lower.

Duplexes with J opposite the natural pyrimidines were also relatively high melting, with Tms again generally higher than those observed for the two duplexes containing G-T wobbles. Tms for duplexes with J opposite the standard nucleobases were compared to the Tms of duplexes with standard purine-pyrimidine pairings (FIG. 4c). The Tms for duplexes with J opposite the natural pyrimidines were more tightly clustered than Tms of either A or G opposite the natural pyrimidines. Tms of duplexes with J opposite the natural purines were also measured. Interestingly, Tms for duplexes with J opposite G were very close to Tms for duplexes with J opposite the natural pyrimidines. This result suggests that J functions not only as a degenerate nucleobase against pyrimidines C and T, but also against purine G.

Nucleobase analogs F and J, commercially available components of an additional base pair, performed as degenerate bases opposite R or Y polymorphic sites, as predicted by base pairing conformational analysis. Additionally, J functioned as a degenerate base opposite B (C, T, and G) polymorphic sites. While not being bound by any theory, this unexpected inclusion of G in the set of suitable target nucleobases for C and T (but not for G without a tendency to tautomerize under certain conditions) is believed to occur because J has well-established tautomeric ambiguity and can form an N3-H tautomer (Groebke et al., Warum pentose- und nicht hexose-nucleinsauren, Helv. Chim. Acta. 81:375-474 (1998); Battersby et al., A new mode of DNA duplex association: Watson-Crick interaction of all-purine deoxyribonucleic acids. Submitted (2006)) that has unusual stability opposite purine G.

Paradoxically, J and F nucleobases can increase specificity of nucleic acid hybridization when introduced as a third base pair (Collins et al., A branched DNA signal amplification assay for quantification of nucleic acid targets below 100 molecules/mL. Nucleic Acids Res. 25:2979-2984 (1997)), yet the individual analogs produce decreased hybridization selectivity opposite the natural nucleobases. Although the analogs when acting as degenerate bases form relatively stable "mismatches" with two or more standard nucleobases, there is still an energy gap between these pairs and the F-J pair. In fact, the F-J pair generally stabilizes a duplex even more than the canonical pairs, helping to maintain a significant gap (Horn et al., Hybridization properties of the 5-methyl-isocytidine/isoguanosine base pair in synthetic oligonucleotides. Tetrahedron Lett. 36:2033-2036 (1995); Roberts et al., Theoretical and experimental study of isoguanine and isocytosine: base pairing in an expanded genetic system. J. Am. Chem. Soc. 119:4640-4649 (1997)).

Example 2

Genotyping Using Degenerate Nucleobase Probes

A degenerate nucleobase probe according to the present invention was generated for the purpose of distinguishing HCV genotype 2 from all other genotypes. The probe sequence was designed to be useful in a probe melting assay following a PCR amplification step of the 5'-UTR of the HCV genome. Such an assay would use melting temperatures (Tms) of a degenerate probe (J Probe, Table 4) bound to a target sequence to detect if that sequence is genotype 2 or non-genotype 2. An examination of melting temperatures against synthetic DNA oligonucleotides was used to verify the utility of the J Probe.

Synthesis of Oligonucleotides. Oligodeoxyribonucleotides were synthesized on a 394 DNA synthesizer (Applied Biosystems) and purified by reversed phase HPLC using the Wave system (Transgenomic). ODN mass was verified as within 0.5% of the expected mass by MALDI-TOF mass spectrometry using a Voyager-DE (Applied Biosystems). ODN purity was >93% by electrophoresis in a polyacrylamide-filled capillary on a $^{3D}$CE instrument (Agilent).

Melting Temperature Determinations. For the melting temperature experiments, duplexes of target and probe were made at 6.25 μM stock in 10 mM Tris, 0.1 mM EDTA, pH 8.5. For each replicate in denaturation experiments a duplex was diluted to 125 nM in AmpliTaq Gold buffer (Applied Biosystems) containing 5 mM $MgCl_2$. Two replicates (50 μL) of each sample were added to a microplate and placed in an MX4000 (Stratagene). The samples were denatured at 95° C. for 1 min and then rapidly cooled to 70° C. FAM fluorescence was continuously acquired while cooling −11.0° C. every 30 s to 20° C. The fluorescence data from denaturation experiments were fitted using cubic smoothing splines. $T_m$s were determined as the maximum of the first derivative of the fitted curve.

Seven target sequences, representative of each of genotypes 1-6 (shown in Table 3, below), were synthesized to test the system. Two target sequences of genotype 2 (2.1 and 2.2) were synthesized because a single position in the target region is polymorphic for C or T in genotype 2 sequences. The remaining five sequences are not meant to capture all of the sequence variation possible in this region among the other genotypes; rather, they represent sequence motifs for each genotype that were subjectively determined to be close in sequence to genotype 2.

TABLE 3

Synthetic oligonucleotides representing targets of genotypes 1-6.

| Target | Sequence | |
|---|---|---|
| Genotype 2.1 | TCCAAGAAAGGACCCAGTCTTCCCGGCAATT | (SEQ ID NO: 3) |
| Genotype 2.2 | TCCAAGAAAGGACCCAGTCTTTCCGGCAATT | (SEQ ID NO: 4) |
| Genotype 1 | TCCAAGAAAGGACCCGGTCGTCCTGGCAATT | (SEQ ID NO: 5) |
| Genotype 3 | TCCAAGAAAGGACCCGGTCAACCCGGCGATT | (SEQ ID NO: 6) |

TABLE 3-continued

Synthetic oligonucleotides representing targets of genotypes 1-6.

| Target | Sequence | |
|---|---|---|
| Genotype 4 | TCCAAGAAAGGACCCGGTCATCCCGGCGATT | (SEQ ID NO: 7) |
| Genotype 5 | TCCAAGAAAGGACCCGGTCATCCCGGCAATT | (SEQ ID NO: 8) |
| Genotype 6 | TCCAA*TG*GAAAGGACCCGGTCATCCTGGCAATT | (SEQ ID NO: 9) |

(Variable positions between the targets are in bold.
An insertion is in italics.
The probe binding region is indicated by underline.)

Three different probes (shown in Table 4) were generated for use in hybridizing to the synthetic oligonucleotide targets shown in Table 3. A first probe (J Probe) uses isoguanine (J) as a degenerate nucleobase opposite the site that can be either C or T in genotype 2. The degenerate J nucleobase allows the probe to be non-selective for genotype 2 with either C or T at the variable position and results in Tms depressed only slightly from Tms observed for targets and perfectly matched probes. The degenerate probe J hybridizes substantially equivalently to genotypes 2.1 and 2.2 and does not help to distinguish genotype 2 from the remaining genotypes, which all have C at the variable position. Two additional probes were generated, one that perfectly matched genotype 2.1 (G Probe) and another that perfectly matches genotype 2.2 (A Probe), as shown below in Table 4.

TABLE 4

Probes used in melting experiments.

| Probe | Sequence | |
|---|---|---|
| JProbe | FAM-GJAAGACTGGGTCCT-BHQ | (SEQ ID NO: 10) |
| GProbe | FAM-GGAAGACTGGGTCCT-BHQ | (SEQ ID NO: 11) |
| AProbe | FAM-GAAAGACTGGGTCCT-BHQ | (SEQ ID NO: 12) |

A summary of data from melting experiments (Table 5) demonstrates the performance of the single J probe. When a fluorescently-labeled probe that perfectly matched the genotype 2.1 target (G probe) was used in melting experiments, the $\Delta T_m$ between genotype 2.1 target and genotype 2.2 target was 3.65° C. When a probe that perfectly matched genotype 2.2 target was used, the $\Delta T_m$ between genotype 2.1 target and genotype 2.2 target was 4.95° C. However, the degenerate J probe was virtually non-selective, with a $\Delta T_m$ between genotype 2.1 target and genotype 2.2 target of only 1.5° C. The $T_m$s for both genotype 2 targets with the J probe were only slightly depressed from the $T_m$s observed for each of the genotype 2 targets against its perfectly matched probe. Also advantageous was the increase in the gap between the highest melting target among the non-genotype 2 sequences and the lowest Tm of the genotype 2 targets observed with J probe. These gaps for G probe and A probe were 9.8° C. and 10.15° C., respectively, and the gap for J probe increased to 12.5° C. All of these characteristics facilitate distinguishing the two genotype 2 targets from the non-genotype 2 targets.

TABLE 5

Mean $T_m$s (n = 2) of target sequences with each of the three probes.

| Probe | Target | Mean $T_m$ | Standard Deviation |
|---|---|---|---|
| A | 2.1 | 53.95 | 0.07 |
| A | 2.2 | 58.9 | 0.00 |
| A | 1 | 43.8 | 0.00 |
| A | 3 | 24.45 | 2.19 |
| A | 4 | 28.3 | 2.12 |
| A | 5 | 29.4 | 1.98 |
| A | 6 | 40.1 | 1.41 |
| G | 2.1 | 60.45 | 0.64 |
| G | 2.2 | 56.8 | 0.00 |

TABLE 5-continued

Mean $T_m$s (n = 2) of target sequences with each of the three probes.

| Probe | Target | Mean $T_m$ | Standard Deviation |
|---|---|---|---|
| G | 1 | 47 | 0.00 |
| G | 3 | 29 | 0.00 |
| G | 4 | 36.9 | 0.14 |
| G | 5 | 37.4 | 0.57 |
| G | 6 | 44.9 | 0.00 |
| J | 2.1 | 57.9 | 0.00 |
| J | 2.2 | 56.4 | 0.57 |
| J | 1 | 43.9 | 0.14 |
| J | 3 | 24.5 | 0.85 |
| J | 4 | 31.4 | 0.57 |
| J | 5 | 32.5 | 0.71 |
| J | 6 | 41.8 | 0.00 |

Example 3

Quantitative Reverse Transcription PCR with Degenerate Probes

A potential use of degenerate probes containing J and F was illustrated in a model quantitative reverse transcription PCR (RT-PCR) assay for hepatitis C virus (HCV).

Primers and Probes. Primers were obtained from Operon Biotechnologies with reversed phase HPLC purification. Probes containing only standard nucleotides were obtained from Biosearch Technologies with anion exchange and reversed phase HPLC purification. Probes containing F or J were synthesized, purified and characterized as described above for melting temperature ODNs. All probes were 5'-labeled with 6-fluorescein and 3'-labeled with Black Hole Quencher 1.

```
Forward primer:
5'-CCATGAATCACTCCCCTGTGAGGAACT-3'   (SEQ ID NO: 13)

Reverse primer:
5'-GCAAGCACCCTATCAGGCAGTACCACA-3'   (SEQ ID NO: 14)
```

Probes against sense strand of amplicon:

```
5'-TTTCGCAACCCAACGCTACTCGGCT-3'     (SEQ ID NO: 15)

5'-TTTCGCGACCCAACACTACTCGGCT-3'     (SEQ ID NO: 16)

5'-TTTCGCJACCCAACJCTACTCGGCT-3'     (SEQ ID NO: 17)
```

Probes against antisense strand of amplicon:

```
5'-AGCCGAGTAGTGTTGGGTCGCGAAA-3'     (SEQ ID NO: 18)

5'-AGCCGAGTAGCGTTGGGTTGCGAAA-3'     (SEQ ID NO: 19)

5'-AGCCGAGTAGFGTTGGGTFGCGAAA-3'     (SEQ ID NO: 20)
```

HCV transcripts were produced from viral samples of subtype 1a, 1b, 2a, and 2b and quantified by phosphate analysis, as described previously by Collins et al., Preparation and characterization of RNA standards for use in quantitative branched DNA hybridization assays, Anal. Biochem. 226, 120-129 (1995)

RT-PCR was conducted in 96-well format at 25 µL. Individual wells contained 1 µL OneStep RT-PCR enzyme mix (Qiagen), 5.0 mM MgCl2, 0.3 mM each deoxynucleoside triphosphate, and 30 nM ROX reference dye (Stratagene) in OneStep RT-PCR buffer. Each reaction contained 400 nM each primer and 125 nM probe. Target levels of 1×103, 1×105, and 1×107 copies of HCV transcript and NTCs were run in triplicate. Amplification was performed on a Stratagene MX3000p with a 50° C. reverse transcription incubation of 40 min, a 95° C. Taq polymerase activation of 15 min, and 40 cycles of 95° C. for 15 s, 67° C. for 1 min, and 72° C. for 30 s. A fixed threshold of 0.04 (dRn) was used to determine CTs. Four 96-well plates were run: 2 with the set of probes to the sense strand of the amplicon, and 2 with the set of probes to the antisense strand of the amplicon. Within each set of probes one plate contained 1a and 2a transcripts as target and the other plate contained 1b and 2b transcripts as target.

This HCV assay resembles molecular diagnostic assays intended for use in clinical laboratories, in which equivalent quantification across subtype samples is desired (Battersby et al., Evaluation of a new assay for quantification of hepatitis C virus (HCV) RNA, Clin. Chem. 51:A175 (2005)). The probe-binding regions of the four HCV transcript targets in these experiments contained two genotype-specific polymorphic sites. Transcripts of subtypes 1a and 1b have a common sequence motif in the probe binding region and transcripts of subtypes 2a and 2b have a different motif with two isolated single base differences in the probe binding region (Table 6). A single probe was used in each of three assays with each HCV transcript: a probe matching the genotype 1 motif, a probe matching the genotype 2 motif, or a degenerate probe to both sequence motifs containing nucleobase analogs. Designing probes specific to the sense and antisense strands of PCR amplicons allowed assessment in separate assays of either F or J as a degenerate nucleobase in the probe.

TABLE 6

Probe binding region targeted in the RT-PCR assay.

| Subtype | Probe binding region | |
|---|---|---|
| 1a and 1b | ---AGCCGAGTAGTGTTGGGTCGCGAAA--- | (SEQ ID NO: 21) |
| 2a and 2b | ---AGCCGAGTAGCGTTGGGTTGCGAAA--- | (SEQ ID NO: 22) |

Targets in the PCR experiments were transcripts generated from different HCV subtypes with a probe binding region containing one of two motifs that correlate with genotype. A single probe was used in each reaction: a probe matching genotype 1, a probe matching genotype 2, or a degenerate probe designed to pair non-selectively with both genotypes. Using a probe matched to one of the two target motifs in quantitative PCR produced a striking difference in $C_T$s with targets of genotype 1 or 2 (Table 7). In fact, when targeting the sense strand of the amplicon, the probe matching genotype 1 failed to generate any signal with genotype 2 as target, and vice versa. In contrast, using the appropriate degenerate probe containing F or J resulted in $C_T$s only slightly higher than the matched probes and near equivalent response with identical amounts of genotype 1 or 2 as target (Table 7).

TABLE 7

ΔC$_T$s for individual probes between targets of different genotypes within a single microplate.

| | ΔC$_T$ | | | | | |
|---|---|---|---|---|---|---|
| | 1a vs 2a | | | 1b vs 2b | | |
| Probe Target | $1 \times 10^7$ | $1 \times 10^5$ | $1 \times 10^3$ | $1 \times 10^7$ | $1 \times 10^5$ | $1 \times 10^3$ |
| Antisense genotype 1 | 8.98 | 7.56 | 8.65 | 5.44 | 4.93 | 5.16 |
| Antisense genotype 2 | 4.97 | 6.01 | 6.12 | 4.99 | 4.44 | 4.57 |
| Antisense F | 0.53 | 0.91 | 0.79 | 0.75 | 0.44 | 0.82 |
| Sense genotype 1 | large | large | large | large | large | large |
| Sense genotype 2 | large | large | large | large | large | large |
| Sense J | −0.55 | −0.65 | −1.25 | −0.47 | −0.24 | −0.22 |

"large" indicates that probes that were not perfectly matched to target failed to produce any signal

What is claimed is:

1. A polynucleotide duplex comprising a degenerate nucleobase oligomer hybridized to a corresponding polynucleotide template,
wherein the corresponding polynucleotide template comprises a first polymorphic site characterized by multiple natural nucleobase variations and a second polymorphic site characterized by multiple nucleobase variations; and
wherein the degenerate nucleobase oligomer has a first polymorphic site characterized by multiple nucleobase variations and a second polymorphic site characterized by multiple nucleobase variations, wherein the oligomer comprises
a degenerate nucleobase complementary to multiple natural nucleobase variations at its first polymorphic site, wherein the degenerate nucleobase is
a pyrimidine or an analog thereof which is complementary to guanine or adenine and has hydrogen-bonding functionality arrayed such that the pyrimidine or analog thereof can form two hydrogen bonds in a wobble conformation with one natural purine and two hydrogen bonds in a reverse wobble conformation with the other natural purine; or
a purine or an analog thereof which is complementary to cytosine, uracil or thymine and has hydrogen-bonding functionality arrayed such that the purine or analog thereof can form two hydrogen bonds in a wobble conformation with one pyrimidine-like component and two hydrogen bonds in a reverse wobble conformation with the other pyrimidine-like component, and
a base-specific nucleobase complementary to a single nucleobase variation at its second polymorphic site, wherein the base-specific nucleobase is characteristic of a single allele of the polynucleotide template;
and wherein the hydrogen bonding pattern of the degenerate nucleobase of the oligomer is pyAAD or puDDA.

2. The polynucleotide duplex according to claim 1, wherein the oligomer comprises a plurality of degenerate nucleobases, each of which is complementary to multiple natural nucleobase variations at a corresponding polymorphic site of the corresponding polynucleotide template.

3. The polynucleotide duplex according to claim 1, wherein a melting temperature of the degenerate nucleobase oligomer and the polynucleotide template is substantially equivalent to a melting temperature of a natural nucleobase oligomer and the polynucleotide template.

4. The polynucleotide duplex according to claim 1, wherein the degenerate nucleobase of the oligomer is flanked by natural nucleobases.

5. The polynucleotide duplex according to claim 1, wherein the hydrogen bonding pattern of the degenerate nucleobase with a corresponding nucleobase of the polynucleotide template is puDDA:pyDAA, puDDA:pyADA, puDA:pyAAD, or puADD:pyAAD.

6. The polynucleotide duplex according to claim 1, wherein the degenerate nucleobase having a hydrogen bonding pattern of pyAAD is 5-methylisocytidine, isocytidine, or 2'-deoxy analogs thereof.

7. The polynucleotide duplex according to claim 1, wherein the degenerate nucleobase having a hydrogen bonding pattern of puDDA is isoguanosine, 7-deazaisoguanosine, 7-deaza-8-azaisoguanosine, N6-(6-aminohexyl)isoguanosine, N6-(2-(1H,imidazol-4-y1)-ethyl)isoguanosine, N6-(N-(Dabcy 1)-6-aminohexyl)isoguanosine, or 2'-deoxy analogs thereof.

8. The polynucleotide duplex according to claim 1, wherein the base-specific nucleobase hybridizes selectively to each allele of a target polymorphic locus.

9. The polynucleotide duplex according to claim 1, wherein the base-specific nucleobase is non-complementary to a single allele of a polymorphic locus.

10. The polynucleotide duplex according to claim 1, wherein the base-specific nucleobase is complementary to a single allele of a polymorphic locus.

* * * * *

UNITED STATES PATENT AND TRADEMARK OFFICE
CERTIFICATE OF CORRECTION

PATENT NO. : 9,677,123 B2  
APPLICATION NO. : 12/282180  
DATED : June 13, 2017  
INVENTOR(S) : Thomas R. Battersby It is certified that error appears in the above-identified patent and that said Letters Patent is hereby corrected as shown below:

In the Claims

1) In Claim 1, Column 53, Line 18, please insert --multi-allelic-- after "corresponding"
2) In Claim 1, Column 53, Line 20, please insert --multi-allelic-- after "corresponding"
3) In Claim 1, Column 53, Line 51, please delete "nucleobasc" and insert --nucleobase--
4) In Claim 2, Column 54, Line 20, please insert --multi-allelic-- after "corresponding"
5) In Claim 5, Column 54, Line 31, please delete "a" and insert --the--.

Signed and Sealed this  
Twenty-fourth Day of October, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 22

<210> SEQ ID NO 1
<211> LENGTH: 15
<212> TYPE: DNA
<213> ORGANISM: Hepatitis C virus
<220> FEATURE:
<221> NAME/KEY: misc_feature
<222> LOCATION: (8)..(8)
<223> OTHER INFORMATION: n is a, c, g, or t

<400> SEQUENCE: 1
cagtaggntc tcccg                                                        15

<210> SEQ ID NO 2
<211> LENGTH: 15
<212> TYPE: DNA
<213> ORGANISM: Hepatitis C virus
<220> FEATURE:
<221> NAME/KEY: misc_feature
<222> LOCATION: (8)..(8)
<223> OTHER INFORMATION: n is a, c, g, or t

<400> SEQUENCE: 2
gtcatccnag agggc                                                        15

<210> SEQ ID NO 3
<211> LENGTH: 31
<212> TYPE: DNA
<213> ORGANISM: Hepatitis C virus

<400> SEQUENCE: 3
tccaagaaag gacccagtct tcccggcaat t                                      31

<210> SEQ ID NO 4
<211> LENGTH: 31
<212> TYPE: DNA
<213> ORGANISM: Hepatitis C virus

<400> SEQUENCE: 4
tccaagaaag gacccagtct ttccggcaat t                                      31

<210> SEQ ID NO 5
<211> LENGTH: 31
<212> TYPE: DNA
<213> ORGANISM: Hepatitis C virus

<400> SEQUENCE: 5
```

```
tccaagaaag gacccggtcg tcctggcaat t                                          31
```

<210> SEQ ID NO 6
<211> LENGTH: 31
<212> TYPE: DNA
<213> ORGANISM: Hepatitis C virus

<400> SEQUENCE: 6

```
tccaagaaag gacccggtca acccggcgat t                                          31
```

<210> SEQ ID NO 7
<211> LENGTH: 31
<212> TYPE: DNA
<213> ORGANISM: Hepatitis C virus

<400> SEQUENCE: 7

```
tccaagaaag gacccggtca tcccggcgat t                                          31
```

<210> SEQ ID NO 8
<211> LENGTH: 31
<212> TYPE: DNA
<213> ORGANISM: Hepatitis C virus

<400> SEQUENCE: 8

```
tccaagaaag gacccggtca tcccggcaat t                                          31
```

<210> SEQ ID NO 9
<211> LENGTH: 33
<212> TYPE: DNA
<213> ORGANISM: Hepatitis C virus

<400> SEQUENCE: 9

```
tccaatggaa aggacccggt catcctggca att                                        33
```

<210> SEQ ID NO 10
<211> LENGTH: 15
<212> TYPE: DNA
<213> ORGANISM: Hepatitis C virus

<400> SEQUENCE: 10

```
ggaagactgg gtcct                                                            15
```

<210> SEQ ID NO 11
<211> LENGTH: 15
<212> TYPE: DNA
<213> ORGANISM: Hepatitis C virus

<400> SEQUENCE: 11

```
ggaagactgg gtcct                                                            15
```

<210> SEQ ID NO 12
<211> LENGTH: 15
<212> TYPE: DNA
<213> ORGANISM: Hepatitis C virus

<400> SEQUENCE: 12

```
gaaagactgg gtcct                                                            15
```

<210> SEQ ID NO 13
<211> LENGTH: 27
<212> TYPE: DNA
<213> ORGANISM: Hepatitis C virus

<400> SEQUENCE: 13

```
ccatgaatca ctcccctgtg aggaact                                               27

<210> SEQ ID NO 14
<211> LENGTH: 27
<212> TYPE: DNA
<213> ORGANISM: Hepatitis C virus

<400> SEQUENCE: 14
gcaagcaccc tatcaggcag taccaca                                               27

<210> SEQ ID NO 15
<211> LENGTH: 25
<212> TYPE: DNA
<213> ORGANISM: Hepatitis C virus

<400> SEQUENCE: 15
tttcgcaacc caacgctact cggct                                                 25

<210> SEQ ID NO 16
<211> LENGTH: 25
<212> TYPE: DNA
<213> ORGANISM: Hepatitis C virus

<400> SEQUENCE: 16
tttcgcgacc caacactact cggct                                                 25

<210> SEQ ID NO 17
<211> LENGTH: 25
<212> TYPE: DNA
<213> ORGANISM: Hepatitis C virus

<400> SEQUENCE: 17
tttcgcgacc caacgctact cggct                                                 25

<210> SEQ ID NO 18
<211> LENGTH: 25
<212> TYPE: DNA
<213> ORGANISM: Hepatitis C virus

<400> SEQUENCE: 18
agccgagtag tgttgggtcg cgaaa                                                 25

<210> SEQ ID NO 19
<211> LENGTH: 25
<212> TYPE: DNA
<213> ORGANISM: Hepatitis C virus

<400> SEQUENCE: 19
agccgagtag cgttgggttg cgaaa                                                 25

<210> SEQ ID NO 20
<211> LENGTH: 25
<212> TYPE: DNA
<213> ORGANISM: Hepatitis C virus

<400> SEQUENCE: 20
agccgagtag cgttgggtcg cgaaa                                                 25

<210> SEQ ID NO 21
<211> LENGTH: 25
<212> TYPE: DNA
<213> ORGANISM: Hepatitis C virus
```

```
<400> SEQUENCE: 21
agccgagtag tgttgggtcg cgaaa                                              25

<210> SEQ ID NO 22
<211> LENGTH: 25
<212> TYPE: DNA
<213> ORGANISM: Hepatitis C virus

<400> SEQUENCE: 22
agccgagtag cgttgggttg cgaaa                                              25
```